US011026625B2

(12) United States Patent
Blanchard et al.

(10) Patent No.: US 11,026,625 B2
(45) Date of Patent: Jun. 8, 2021

(54) SYSTEMS AND METHODS FOR TREATING AND ESTIMATING PROGRESSION OF CHRONIC KIDNEY DISEASE

(71) Applicant: Fresenius Medical Care Holdings, Inc., Waltham, MA (US)

(72) Inventors: Thomas C. Blanchard, Somerville, MA (US); Len Usvyat, Boston, MA (US); Yuedong Wang, Santa Barbara, CA (US); Peter Kotanko, New York, NY (US); Dugan W. Maddux, Lincoln, MA (US); Franklin W. Maddux, Lincoln, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 75 days.

(21) Appl. No.: 16/058,965

(22) Filed: Aug. 8, 2018

(65) Prior Publication Data

US 2019/0046112 A1    Feb. 14, 2019

Related U.S. Application Data

(60) Provisional application No. 62/542,633, filed on Aug. 8, 2017.

(51) Int. Cl.
*A61B 5/00* (2006.01)
*G16H 20/10* (2018.01)
(Continued)

(52) U.S. Cl.
CPC ............ *A61B 5/4842* (2013.01); *A61B 5/201* (2013.01); *A61B 5/4839* (2013.01);
(Continued)

(58) Field of Classification Search
CPC combination set(s) only.
See application file for complete search history.

(56) References Cited

U.S. PATENT DOCUMENTS 5,246,835 A    9/1993 Suzuki et al.
5,301,105 A    4/1994 Cummings, Jr.
(Continued)

FOREIGN PATENT DOCUMENTS

AU    2017201885 A1    10/2017
AU    2017218008 A1    10/2018
(Continued)

OTHER PUBLICATIONS

International Search Report and Written Opinion for application No. PCT/US2018/045871, dated Jul. 12, 2018, 13 pages.
(Continued)

*Primary Examiner* — Paula J Stice
(74) *Attorney, Agent, or Firm* — Kacvinsky Daisak Bluni PLLC

(57) ABSTRACT

Exemplary systems and methods for estimating progression of chronic kidney disease in a patient and applying clinical interventions may include determining historic values of at least one patient parameter that varies as a function of the progression of the chronic kidney disease over time, and computationally estimating a trend corresponding to the historic values. Based on the trend, at least one marker may be automatically provided that identifies a clinical intervention and a time in the future when the clinical intervention is expected to be needed. Based on the at least one marker, clinical preparations may be executed at a time prior to the administration of the intervention in order to improve at least one of a) timeliness of the execution of the intervention and b) effectiveness of the intervention.

14 Claims, 18 Drawing Sheets

| Marker | eGFR | CKD Stage | Action |
|---|---|---|---|
| Education & interventions to slow CKD progression | eGFR 30-60 | 3a and 3b | Education to slow progression |
| Nutritional counseling and referral to dietician when feasible | eGFR <60 | 3a CKD 3, 4 and 5 | Referral to RD when feasible, recommend online resources |
| Vaccinations | eGFR <60 | 3a CKD 3, 4 and 5 | Provide and document CDC recommended vaccinations for CKD |
| Referral to nephrology | eGFR <30 or >30 with proteinuria or uncontrolled HTN | 4 and 5 or with proteinuria or uncontrolled HTN | Referral to nephrology |
| Referral for primary renal transplant | eGFR 25-30 | 4 | nephrologist assess for transplant candidacy and preemptive transplant referral made if appropriate |
| Modality Choice | eGFR <=20 | Late Stage 4 | Treatment decision made & documented |
| Permanent Access Referral | eGFR <20 | Late Stage 4 | Permanent vascular access referral |
| Functional, usable permanent access | eGFR <20 | Late Stage 4 | Maintenance of a usable permanent access pending dialysis start |
| Coordinate Start of RRT | At dialysis start | nephrologist discretion | Planned optimal start |
| Unprepared best start of dialysis | Urgent start | | Unprepared best start |

(51) Int. Cl.
  *A61M 1/16* (2006.01)
  *G16H 50/20* (2018.01)
  *A61B 5/20* (2006.01)
  *A61M 1/28* (2006.01)

(52) U.S. Cl.
  CPC ............ *A61B 5/7275* (2013.01); *A61B 5/743* (2013.01); *A61M 1/1603* (2014.02); *A61M 1/28* (2013.01); *G16H 20/10* (2018.01); *G16H 50/20* (2018.01); *A61M 2205/3303* (2013.01)

(56) References Cited

U.S. PATENT DOCUMENTS

| | | | |
|---|---|---|---|
| 5,307,262 | A | 4/1994 | Ertel |
| 5,519,607 | A | 5/1996 | Tawil |
| 6,447,989 | B1 | 9/2002 | Comper |
| 7,383,239 | B2 | 6/2008 | Bonissone et al. |
| 7,676,379 | B2 | 3/2010 | Kil et al. |
| 7,739,129 | B2 | 6/2010 | Sweetland et al. |
| 8,655,675 | B2 | 2/2014 | Kil et al. |
| 8,682,696 | B1 | 3/2014 | Shanmugam |
| 8,930,209 | B2 | 1/2015 | Biedermann |
| 9,251,310 | B2 | 2/2016 | McNally et al. |
| 9,689,826 | B2 | 6/2017 | Haick et al. |
| 2002/0012906 | A1 | 1/2002 | Comper |
| 2003/0003588 | A1 | 1/2003 | Comper |
| 2004/0024042 | A1 | 2/2004 | Breyer |
| 2004/0122708 | A1 | 6/2004 | Avinash et al. |
| 2004/0241774 | A1 | 12/2004 | Kazuo |
| 2005/0214294 | A1 | 9/2005 | Flyvbjerg et al. |
| 2007/0037232 | A1 | 2/2007 | Barasch et al. |
| 2007/0050215 | A1 | 3/2007 | Kil et al. |
| 2009/0228301 | A1 | 9/2009 | Youngblood et al. |
| 2010/0081148 | A1 | 4/2010 | Singbartl et al. |
| 2010/0144684 | A1 | 6/2010 | Bishop |
| 2010/0234765 | A1 | 9/2010 | Barasch et al. |
| 2011/0077958 | A1 | 3/2011 | Breitenstein et al. |
| 2011/0183434 | A1 | 7/2011 | Wolf |
| 2012/0058934 | A1 | 3/2012 | Bar-Or |
| 2012/0072231 | A1 | 3/2012 | Mayer et al. |
| 2012/0129265 | A1 | 5/2012 | Lundin et al. |
| 2012/0164662 | A1 | 6/2012 | Hara et al. |
| 2012/0191467 | A1 | 7/2012 | LaPlante et al. |
| 2012/0195876 | A1 | 8/2012 | Reiser |
| 2012/0255044 | A1 | 10/2012 | Matsuo et al. |
| 2012/0303381 | A1 | 11/2012 | Bessette |
| 2012/0329015 | A1 | 12/2012 | Thesman |
| 2013/0052206 | A1 | 2/2013 | Agnello |
| 2013/0061436 | A1 | 3/2013 | Peters et al. |
| 2013/0078655 | A1 | 3/2013 | Bradwell |
| 2013/0143806 | A1 | 6/2013 | Nelsestuen |
| 2013/0210861 | A1 | 8/2013 | Shukla et al. |
| 2013/0262357 | A1 | 10/2013 | Amarasingham et al. |
| 2013/0345175 | A1 | 12/2013 | Beisswenger |
| 2014/0121158 | A1 | 5/2014 | Bar-Or et al. |
| 2015/0106123 | A1 | 4/2015 | Amarasingham et al. |
| 2015/0201878 | A1 | 7/2015 | Chen et al. |
| 2015/0219670 | A1 | 8/2015 | McConnell et al. |
| 2015/0220698 | A1* | 8/2015 | Argyropoulos ........ G01N 33/78 705/3 |
| 2015/0317743 | A1 | 11/2015 | Flam et al. |
| 2016/0034619 | A1 | 2/2016 | Peyerl et al. |
| 2016/0085919 | A1 | 3/2016 | Sohr et al. |
| 2016/0116486 | A1 | 4/2016 | Perichon et al. |
| 2016/0187348 | A1 | 6/2016 | Yerramilli et al. |
| 2016/0216278 | A1 | 7/2016 | McConnell et al. |
| 2016/0292391 | A1 | 10/2016 | Fink et al. |
| 2016/0313342 | A1 | 10/2016 | Hamase et al. |
| 2016/0357923 | A1 | 12/2016 | Dong et al. |
| 2017/0016914 | A1 | 1/2017 | Dockrell et al. |
| 2017/0030929 | A1 | 2/2017 | Lemke et al. |
| 2017/0034144 | A1 | 2/2017 | Kisters |
| 2017/0061093 | A1 | 3/2017 | Amarasingham et al. |
| 2017/0115310 | A1 | 4/2017 | Colhoun et al. |
| 2017/0219582 | A1 | 8/2017 | Sidhu et al. |
| 2017/0228506 | A1 | 8/2017 | Nadkarni et al. |
| 2017/0228507 | A1 | 8/2017 | Bottinger et al. |
| 2017/0239211 | A1 | 8/2017 | Youn et al. |
| 2017/0269101 | A1 | 9/2017 | Yerramilli et al. |
| 2017/0290551 | A1 | 10/2017 | An et al. |
| 2017/0320854 | A1 | 11/2017 | Collin et al. |
| 2018/0100866 | A9 | 4/2018 | Barasch et al. |
| 2018/0164327 | A1 | 6/2018 | Kikuchi et al. |
| 2018/0166174 | A1 | 6/2018 | Lewis |
| 2018/0271885 | A1 | 9/2018 | White et al. |
| 2019/0017119 | A1 | 1/2019 | Khera et al. |
| 2019/0033288 | A1 | 1/2019 | Mostafa et al. |
| 2019/0041402 | A1 | 2/2019 | Sidhu et al. |
| 2019/0060320 | A1 | 2/2019 | Meinicke et al. |
| 2019/0066843 | A1 | 2/2019 | Carlson |
| 2019/0069815 | A1 | 3/2019 | Burnes et al. |
| 2019/0088356 | A1 | 3/2019 | Oliver et al. |
| 2019/0122770 | A1 | 4/2019 | Pengetnze et al. |
| 2019/0125901 | A1 | 5/2019 | Debreczeny et al. |
| 2019/0125902 | A1 | 5/2019 | Rajagopalan et al. |
| 2019/0156919 | A1 | 5/2019 | Magis et al. |
| 2020/0292558 | A1 | 9/2020 | Van Eyk et al. |

FOREIGN PATENT DOCUMENTS

| | | |
|---|---|---|
| AU | 2016417160 A1 | 3/2019 |
| CN | 102526324 A | 7/2012 |
| CN | 105712983 A | 6/2016 |
| CN | 106556703 A | 4/2017 |
| CN | 107919170 A | 4/2018 |
| EP | 3334498 A1 | 6/2018 |
| EP | 3471107 A1 | 4/2019 |
| JP | 2008191135 A | 8/2008 |
| JP | 3599895 B2 | 6/2010 |
| JP | 6082446 B2 | 6/2010 |
| JP | 2010139429 A | 6/2010 |
| MX | 2015003851 A | 9/2016 |
| RU | 2646467 C1 | 3/2018 |
| WO | 2012167186 A1 | 12/2012 |
| WO | 13096740 A1 | 6/2013 |
| WO | 13122469 A2 | 8/2013 |
| WO | 13124478 A1 | 8/2013 |
| WO | 15070041 A1 | 5/2015 |
| WO | 2017004880 A1 | 3/2017 |
| WO | 17089979 A1 | 6/2017 |
| WO | 18210449 A1 | 11/2018 |

OTHER PUBLICATIONS

Anonymous, "CKD-EPI Creatinine Equation (2009)", National Kidney Foundation [online], Jan. 2009 [retrieved on Feb. 6, 2019]. Retrieved from the Internet URL: https://www.kidney.org/content/ckd-epi-creatinine-equation-2009, 3 pages.

* cited by examiner

SYSTEMS AND METHODS FOR TREATING AND ESTIMATING PROGRESSION OF CHRONIC KIDNEY DISEASE

CROSS-REFERENCE TO RELATED APPLICATIONS

This application claims priority to U.S. Provisional Patent Application Ser. No. 62/542,633, filed Aug. 8, 2017, entitled "Systems and Methods for Predicting and Treating Progression of Chronic Kidney Disease," the contents of which application is expressly incorporated by reference herein.

FIELD

The disclosure generally relates to healthcare related systems, devices, and methods.

BACKGROUND

Traditional health care systems are based on a fee-for-service model, whereby healthcare providers are compensated on a per-treatment or per-service basis. Under this model, a healthcare provider's compensation increases when the number of provided treatments or services increases. As such, there is no financial incentive for such providers to efficiently manage the number of provided services/procedures, nor is there any financial incentive related to the overall health outcome of the patient. Such traditional systems have led to spiraling healthcare costs and inefficiencies hindering the quality of overall care of the patient.

Moreover, many patients—especially patients with chronic illnesses—engage with a variety of different entities and health care professionals in the course of their diagnosis, treatment, and long-term care management, including hospitals, clinics, laboratories, pharmacies, physicians, clinicians, and/or other specialists. The patients' treatment information may be spread across several entities, repositories, and medical professionals, which can lead to lack of communication, or miscommunication, between the various involved entities, which can detrimentally affect the treatment and health of the patient, possibly even creating life-threatening treatment conditions. Further, this uncoordinated handling of data, and the patient's overall treatment, results in inefficiencies that can lead to increased total cost of care. In this regard, traditional fee-for-service healthcare models are far from ideal with respect to care quality and economics. The latter is evidenced by the untenable continued rise in healthcare costs in the United States under the fee-for-service model.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the present disclosure. The present disclosure may include the following various aspects and embodiments.

An exemplary embodiment of a method for estimating progression of chronic kidney disease in a patient and applying clinical interventions may include determining historic values of at least one patient parameter that varies as a function of the progression of the chronic kidney disease over time, and computationally estimating a trend corresponding to the historic values. Based on the trend, at least one marker may be automatically provided that identifies a clinical intervention and a time in the future when the clinical intervention is expected to be needed. Based on the at least one marker, clinical preparations may be executed at a time prior to the administration of the intervention in order to improve at least one of a) timeliness of the execution of the intervention and b) effectiveness of the intervention.

According to various of the foregoing and other embodiments of the present disclosure, the method may further include calculating predicted future values of the at least one patient parameter based on the trend. The method may further include incorporating into a visual chart the at least one marker and at least one of a) the trend and b) the predicted future values of the at least one patient parameter calculated based on the trend. The executing clinical preparations may include providing treatment options to the patient and executing the intervention according to a corresponding treatment decision made by the patient. The at least one patient parameter may include an estimated glomerular filtration rate (eGFR). The trend may computationally estimated by non-linear regression. The trend may be computationally estimated by linear regression.

An exemplary embodiment of a method for estimating progression of chronic kidney disease in a patient and applying clinical interventions may include determining historic values of at least one patient parameter that varies as a function of the progression of the chronic kidney disease over time, and computationally estimating a trend corresponding to the historic values. predicted future values of the at least one patient parameter may be calculated based on the trend. Based on the trend, at least one marker may be automatically provided that identifies a clinical intervention and a time in the future when the clinical intervention is expected to be needed. The historic and the predicted future values of the at least one patient parameter and the at least one marker may be incorporated for visualization of the disease progression and treatment options. The treatment options may be provided to the patient based on the progression estimation.

According to various of the foregoing and other embodiments of the present disclosure, the at least one marker may be automatically provided at a location relative to the trend that corresponds to predetermined values of the at least one patient parameter. The at least one patient parameter may be an estimated glomerular filtration rate (eGFR). The historic values of at least one patient parameter may be determined based on information received from a remote source, the information received being at least one of a) the historic values of the at least one patient parameter, and b) data for calculating the historic values of the at least one patient parameter. The treatment options may include interventional treatment for the patient to address the disease progression. The method may further include generating a report including the incorporated historic values and the predicted future values of the at least one patient parameter and the one or more markers, and accessing the report for providing the treatment options to the patient. The method may further include calculating actual values of the at least one patient parameter, comparing the actual values to the predicted future values, and adjusting the treatment options in response to a deviation between the actual values and the predicted future values.

An exemplary embodiment of a system for estimating kidney disease progression and providing automatic treatment options based on the progression estimation may include an integrated care system. The system may be configured to determine historic values of at least one patient parameter that varies as a function of the progression of the chronic kidney disease over time, and computationally estimate a trend corresponding to the historic values. Based on the trend, the system may be configured to automatically provide at least one marker that identifies a clinical intervention and a time in the future when the clinical intervention is expected to be needed. The system may be configured to cause clinical preparations to be conducted at a time prior to the administration of the intervention in order to improve at least one of a) timeliness of the execution of the intervention and b) effectiveness of the intervention.

According to various of the foregoing and other embodiments of the present disclosure, the at least one patient parameter may be an estimated glomerular filtration rate (eGFR). The historic values of at least one patient parameter may be determined based on information received from an outside system, the information received being at least one of a) the historic values of the at least one patient parameter, and b) data for calculating the historic values of the at least one patient parameter. The system may be configured to identify treatment options for presentation to the patient. The system may be configured to calculate predicted future values of the at least one patient parameter based on the trend; generate a report that may include the incorporated historic and the predicted future values of the at least one patient parameter and the one or more markers; and access the report for identifying the treatment options for presentation to the patient. The system may be configured to calculate actual values of the at least one patient parameter; compare the actual values to respective estimated future values; and adjust the treatment options for presentation to the patient in response to a deviation between the actual values and the estimated future values.

Further features and aspects are described in additional detail below with reference to the appended Figures.

BRIEF DESCRIPTION OF THE DRAWINGS

By way of example, embodiments of the disclosed methods and devices will now be described, with reference to the accompanying drawings, in which.

DETAILED DESCRIPTION

Figure 1A:
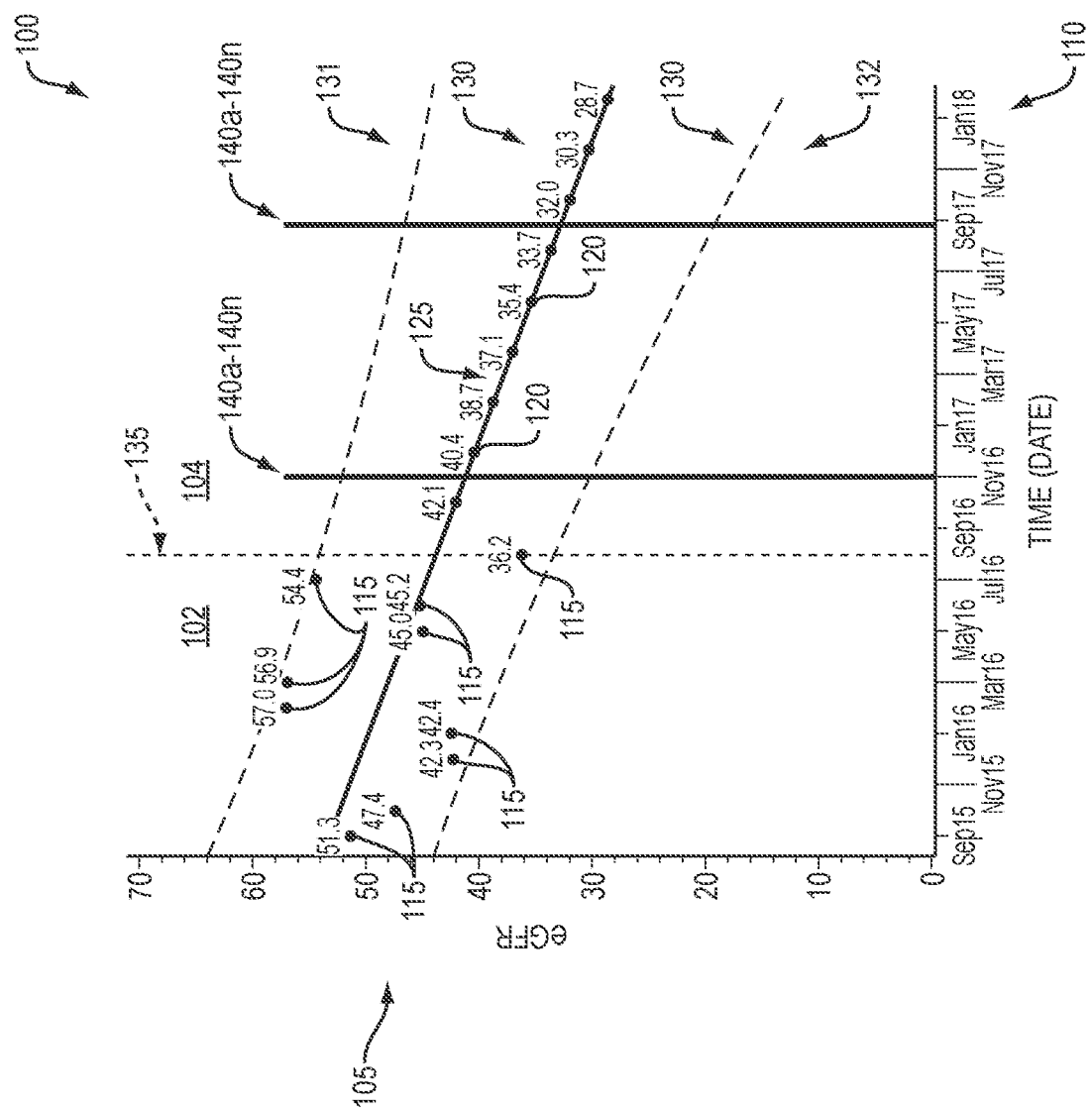
FIG. 1A is a chart illustrating an exemplary embodiment of a method for estimating and treating progression of CKD in accordance with the present disclosure.

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices, diagnostics, and treatments for various diseases, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Example embodiments described herein are suitable for implementing value-based care, which is an alternative to the conventional fee-for-service healthcare model. Under a value-based healthcare system (also known as a "pay for performance" model), healthcare providers are provided with financial incentives tied to quality and efficiency of care and patient outcomes.

Some example embodiments are configured to provide coordinated care to a population of patients with a chronic disease, such as chronic kidney disease (CKD). CKD is a progressive disease marked by reduced kidney function. Once the kidney function drops below a threshold, the patient is considered to have kidney failure, or end-stage renal disease (ESRD). ESRD is the final stage of CKD and requires dialysis treatments for the remainder of the patient's life (absent a transplant).

In the United States, one model of value-based care in which example embodiments described herein may be implemented is the Comprehensive ESRD Care (CEC) Model, which is a type of accountable care organization (ACO) model developed under the authority of the U.S. Center for Medicare and Medicaid Innovation. In order to implement the CEC model, ESRD Seamless Care Organizations (ESCOs) are formed. An ESCO is an ACO that is formed by healthcare suppliers and providers voluntarily coming together. The resulting ESCO is a legal entity that provides coordinated care to ESRD beneficiaries through the CEC model.

Under the ESCO model, the ESCO shares savings and losses incurred by the U.S. Centers for Medicare and Medicaid Services (CMS) for the ESCO's beneficiaries. Savings or losses are determined by CMS based on an expenditure benchmark, which is derived from a baseline that reflects historical expenditure data for like or similar beneficiaries. The benchmark is compared to the actual Medicare Fee-For-Service (FFS) Part A and B expenditures for the aligned patient population in a performance year. The savings are also subject to an adjustment based on quality performance. Any reduction in costs directly translates to increased shared savings (profits), since the costs are measured against the predetermined benchmark. Quality of care is incentivized by the quality performance adjustment to the calculated shared savings.

The ESCO is responsible for each patient's overall care, which goes beyond dialysis treatments. For example, if a patient is admitted to the hospital for any reason (for example, infections, vascular dialysis access complications, and/or cardiac complications), the cost of the hospitalization counts against the yearly savings calculation. Since hospital admissions are especially costly, it is highly advantageous for ESCOs to keep the patients out of the hospital from a financial perspective. Example embodiments described herein implement a holistic approach to oversee and manage all aspects of the patients' well-being, which improves the quality of care while increasing efficiency of medical resources and overall cost efficiency.

Some example embodiments described herein analyze medical data of the applicable patient population in order to target high-risk patients with interventions to reduce the likelihood of hospitalization. Some examples analyze patient data to predict when a patient is likely to experience a particular health-related event or stage of disease progression and provide/adjust treatment accordingly.

In accordance with example embodiments, patient information may be sent to, managed within, and/or be accessible by, a coordinated care system, so that patients may receive high quality, efficient, coordinated health-care within a managed system that is able to intelligently manage and coordinate the patient's overall care. Incorporation of a coordinated care system may allow for better control of health care costs, e.g., by providing value-based care to patients in place of fee-for-service care. For example, as mentioned above, the population of patients diagnosed with ESRD has been increasing over time, often caused by several other diseases, including but not limited to diabetes, hypertension, and/or glomerulonephritis. Patients living with ESRD may face additional challenges due to the nature of the disease. For example, required lifestyle changes may lead to mental health deterioration. Additionally, at-home treatments may lead to increased isolation from medical professionals. As the healthcare landscape changes, opportunities to provide patients with resources for coordinating treatment may deliver additional patient health benefits beyond dialysis treatment.

Although exemplary embodiments described herein are related to renal diseases, it is understood that coordinated care systems and infrastructures described herein may be applicable to other chronic illnesses as an alternative or in addition to renal disease. Such other conditions may include, as non-limiting examples, cardiovascular related illnesses, pulmonary, gastrointestinal, neurological, urological, or gynecological conditions, diabetes, circulatory diseases, Alzheimer's or other dementias, asthma, COPD, emphysema, cancer, obesity, tobacco use, cystic fibrosis, or combinations thereof. Moreover, although some examples are described with respect to implementations in renal-related ACOs, such as ESCOs, it should be understood that the examples described herein may be analogously implemented in other ACOs with respect to other diseases or patient populations, and/or any other suitable value-based healthcare models.

An exemplary embodiment in accordance with the present disclosure may include a system for estimating and treating progression of CKD. As described below, a coordinated care system may be configured for analyzing individual patient information, comparing various patient data in a patient population, determining a treatment intervention, or projecting future treatment interventions, or combinations thereof. For example, the coordinated care system may estimate events associated with CKD and take appropriate action, including but not limited to informing patients, informing clinicians of when specific interventions may be warranted, outlining proposed treatment intervention options, and/or alerting clinicians to upcoming important dates for treatment interventions. Methods described herein may also include preparing for and/or carrying out such interventions in accordance with the coordinated care system's estimations.

Electronic medical records being stored by a patient's primary care physician, specialty physician, or by a third party, e.g., Acumen® Physician Solutions, may be sent to and/or accessible by an integrated care, or a care analysis and guidance, system. The integrated care system may receive, store, and/or determine relevant demographic and laboratory values for calculations, e.g., calculations of historic estimated glomerular filtration rate (eGFR), which is a patient parameter that is indicative of kidney function, which decreases as CKD progresses. The integrated care system may then use the calculated eGFR values to project future eGFR values (see FIG. 1A). It is understood that Glomerular Filtration Rate (GFR) may be an indicator of renal function in a patient.

In some embodiments, as patient parameter information is updated, e.g., data points are included in the system, corresponding future or estimated patient parameters may be updated and adjusted accordingly. As the patient has actual eGFR values measured or determined over time, actual eGFR values will replace the predicted future eGFR values. If the patient has made certain adjustments (e.g., lifestyle, dietary, mental health, and/or other changes), an actual eGFR value may not correspond to a future eGFR value that was estimated. As such, the actual or historic eGFR value may then be included in determining further future eGFR values, which may adjust or altogether alter a timeline and any associated actions.

As shown in FIG. 1A, an integrated care system (e.g., care analysis and guidance system) may receive, store, and/or calculate historic estimated glomerular filtration rate (eGFR) values 115 from information and data in an electronic medical record of a patient. Although eGFR values are described with respect to the chart 100, it is understood that other patient parameters may be utilized in a similar manner to generate a corresponding chart for monitoring patient health and future estimations. For example, patient parameters may include any parameters related to a patient's health, e.g., laboratory values, data, other patient information, or combinations thereof.

In some embodiments, the historic eGFR values 115 may already be stored in the electronic medical records, while in other embodiments the historic eGFR values 115 may be calculatable by components of the integrated care system, based on other data and information provided in the electronic medical records. For example, the EMR may contain laboratory values, physician notes, demographic information, and other information related to a patient's condition. The information may be utilized in determining (e.g., calculating) a historic value for one or more patient parameters.

The integrated care system may then use these historic eGFR values 115 to project future eGFR values 120, e.g., as shown with respect to y-axis 105. For example, a chart 100 may include a marker 135, e.g., a line divider, visually indicating historic, measured values 115 disposed on the left of the marker 135, as indicated by reference numeral 102. Estimated future eGFR values may be disposed on the right of the marker 135, as indicated by reference numeral 104. This may provide a "roadmap" of a patient's future medical treatment recommendations.

The chart 100 may be generated as at least a portion of a report, accessible by medical professionals treating a patient. In some embodiments, historic and future eGFR values may be for an individual patient, for generating a chart 100, or report, and in some embodiments, a chart and/or report may be generated for a patient population. For example, historic and predicted future eGFR values may be aggregated for a patient population for additional analysis. Patient data may be analyzed within a specified demographic (e.g., age, race, national original, geographic location), and/or patients at a specified stage of CKD, for larger data trends, that may provide medical professionals with interventional treatment options for an individual patient having similar population characteristics.

In embodiments where the integrated care system calculates historic eGFR values 115, demographic and measured standardized serum creatinine levels from the patients' electronic medical records may be provided to the integrated care system for analysis. According to the National Kidney Foundation, the Chronic Kidney Disease Epidemiology Collaboration (CKD-EPI) creatinine equation is:

$$eGFR=141 \times \min(S_{Cr}/\kappa,1)^{\alpha} \times \max(S_{Cr}/\kappa,1)^{-1.209} \times 0.993^{Age} \times 1.018[\text{if female}] \times 1.159[\text{if Black}]; \quad (1)$$

where eGFR (estimated glomerular filtration rate)=mL/min/1.73 m$^2$, $S_{Cr}$ (standardized serum creatinine)=mg/dL, $\kappa$=0.7 (females) or 0.9 (males), $\alpha$=−0.329 (females) or −0.411 (males), min=indicates the minimum of $S_{Cr}/\kappa$ or 1, max=indicates the maximum of $S_{Cr}/\kappa$ or 1, and age=years.

Estimated future eGFR values 120 may be based on the historic eGFR values 115, by performing regression on the logarithmic scale. In some embodiments, future eGFR values 120 may be estimated by linear or non-linear regression. For example, the historic eGFR values 115 may be regressed against a time, e.g., a number of days passed, to determine a trend 125 of the historic eGFR values 115. This trend 125 may be relied upon to determine the predicted future eGFR values 120, where the values of $\beta_0$ and $\beta_1$ are determined via least-squares regression:

$$\log(eGFR) \sim \beta_0 + \beta_1 * \text{days} \quad (2)$$

The regression coefficients accordingly are utilized to estimate the future eGFR values 120, which are represented as points along the trend line 125 (i.e., the regression line), as shown in the chart 100 of FIG. 1A. Additionally, the standard error may be used to determine a confidence interval 130 both for the historic eGFR values 115 and the future eGFR values 120. The confidence interval 130 corresponds to broken lines 131 and 132 and the range of values disposed therebetween.

When the historic eGFR values 115 and the predicted future eGFR values 120 have been determined, the integrated care system may utilize this data to provide information to the patient and other medical professionals. For example, the integrated care system may interface with the chart 100 to include a visualization of a patient's CKD progression. For example, the marker, or line divider, 135 may be added to provide a quick visual reference for a medical professional to see where the historic eGFR values 115 end and where the future estimated eGFR values 120 begin. In some embodiments, the confidence interval 130 may be closer to the known historic eGFR values 115 than the future estimated eGFR values 120. For example, the chart 100 may show the confidence interval 130 closer to the historic eGFR values 115 on the measured values side of line divider 135. On the predicted/estimated values side of the line divider 135 the lines showing the confidence interval 130 may expand outward from the trendline 125, indicating a change in confidence interval 130.

As the predicted future eGFR values 120 are estimates, it may be advantageous for the medical professional to see where the estimations begin. The chart 100 may also be interactive with the medical professional, so that a user may click and drag a point along the trend line 125 to see future eGFR values 120. It may be advantageous to the medical professional to plan for a patient's future treatments for scheduling, as well as to the patient for their own education and understanding of the disease trajectory, and to plan for any potential future costs associated with the treatments. It may also be advantageous to proactively anticipate intervention milestones, so that the interventions can be processed and administered efficiently and timely, perhaps affecting the timeline of the patient's CKD progression, and/or potentially reversing patient parameters.

In some embodiments, the chart 100 may also include one or more markers 140a, 140b, . . . 140n, indicating an estimate for when clinical interventions may be necessary. The one or more markers may be an event associated with a predetermined future eGFR value. It is understood that any number "n" of markers may be utilized. For example, a first marker 140a may be placed along the trend line 125 amongst the future eGFR values 120, where the first marker 140a may correspond to a future date. The first marker 140a may indicate that when a patient's eGFR may achieve a value along a trend line at a future date, an action should be performed (see FIG. 1B). The future estimated date may be provided to a medical professional and/or patient for scheduling the appropriate medical treatment, and/or providing immediate interventional treatment to potentially slow or reverse a patient parameter. A second marker 140b, may be further in the future estimation on the trend line 125 in time, e.g., when the patient's eGFR may achieve another value along the trend line 125 at a future estimated date. In embodiments, the second marker 140b may be an indicator or prompt for when an appointment may be made for evaluating the necessity of or creating a permanent access such as a fistula for initiating future dialysis treatment. For example, the second marker 140b may be any time in the future (e.g., weeks and/or months) from the first marker 140a, and based on the future estimated eGFR values 120 and the trend line 125, so as to approximate when the patient may need appropriate medical care. Additionally, the estimated date may allow for a patient to receive immediate interventional treatment based on an estimated timeline. Immediate interventional treatment may benefit a patient's health, as well as provide healthcare providers with timely scheduling and/or an understanding of potential upcoming personnel needs, medications and/or other supply or inventory requirements, or combinations thereof. In some embodiments, immediate interventional treatments to a patient may slow or even reverse patient parameters.

One or more databases may be editable and/or storable in an integrated care system, and may be accessible for analysis. The database may include information associated with the one or more markers 140a, 140b . . . 140n, and may approximate eGFR values assigned for when they should be included in the chart 100. The one or more markers 140a, 140b . . . 140n may be any item in which action should be taken to address a patient's CKD, including but not limited to education and interventions to slow CKD progression 140*a*, nutrition counseling and referral to nutritionist or dietician 140*b*, vaccinations 140*c*, referral to nephrology 140*d*, referral for a primary renal transplant 140*e*, modality choice 140*f*, referral for permanent access procedure 140*g*, maintaining usable permanent access 140*h*, coordination of renal replacement therapy (RRT) 140*i*, e.g., dialysis, an unprepared dialysis start, and a prepared start of dialysis 140*j* (see FIG. 1B).

Figure 1B:
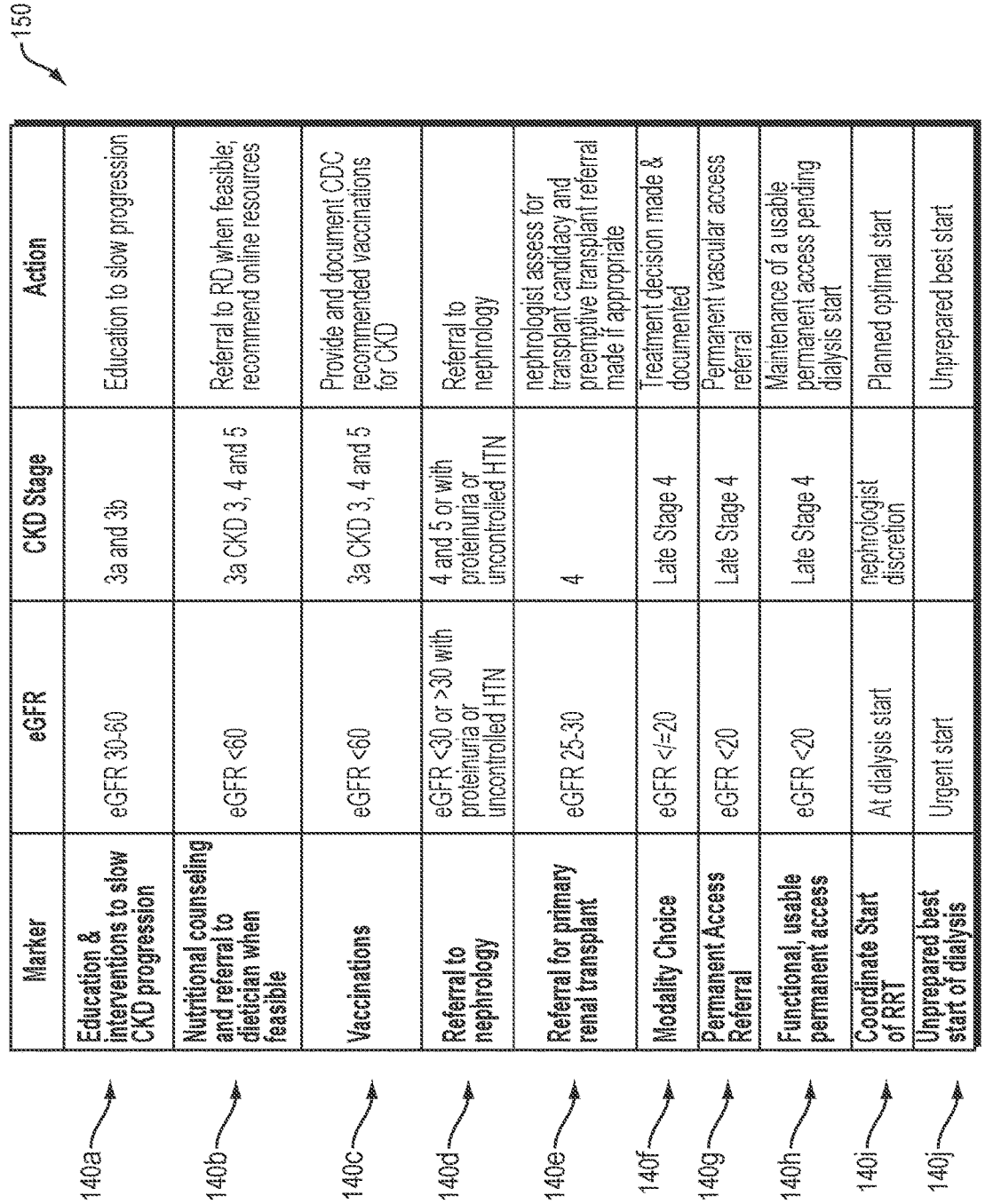
FIG. 1B is a table illustrating an exemplary embodiment of a method for estimating and treating progression of CKD in accordance with the present disclosure.

Referring now to FIG. 1B, a database table illustrating exemplary markers 140*a*, 140*b*, . . . 140*n*, is shown, including approximate eGFR values for applying the selected marker 140*a*, 140*b*, . . . 140*n*, the associated stage of CKD, appropriate action to be taken by a medical professional, or combinations thereof. For example, education and intervention to slow CKD progression may be scheduled at any point when an eGFR value is calculated to be between 30 and 60. An appointment may be made to meet with a medical professional to provide a patient with information regarding diet management, blood pressure management, mental health evaluations, or cardiovascular disease risk management recommendations, or combinations thereof, to potentially slow and/or reverse the progression of kidney disease. In some embodiments, the patient's electronic medical records may include a task that the education and intervention marker is to be completed no later than a minimum eGFR value calculation. For example, if the eGFR value is equal to or below 30 along the trend line 125, the electronic medical record may indicate whether the patient has attended an educational appointment, and if not, may alert at least one of the patient, medical professional, primary care physician, and the like, to schedule the appointment. Alerts may be communicated, e.g., wirelessly, by email, text, voicemail, calendar appointment, app notification, or the like.

In some embodiments, eGFR values may have predetermined values, such that in the event patient parameters equal or fall below the calculated values, interventional treatments, medical consultations, or other diagnostic tests, may be provided to the patient as immediate treatment.

The one or more markers 140*a*, 140*b*, . . . 140*n* may also incorporate best practices and recommendations of other medical organizations, for recommendations to patients with kidney disease, for a total health analysis. For example, another marker may be vaccinations, in that at a predetermined eGFR value, a patient should have been administered vaccinations recommended by the Center for Disease Control (CDC), which recognizes CKD as a high-risk group for infection. The recommendations by the CDC may be integrated into the chart 100 and associated with eGFR values to determine when a patient should have received the recommended vaccinations. In some embodiments, a patient may be scheduled to meet with a dietician or other nutritional expert, which may be incorporated into the chart 100 as well. Other outside systems may be accessible to the integrated care system for obtaining the recommended information so that information may be incorporated into the chart 100, or into some other graph, report, table, tool, etc., or use the information in some other way, e.g., to calculate, model, estimate, and/or alert some activity relevant to the patient's care. The information may also be stored for later use, and/or aggregation for a larger patient population analysis.

In more advanced (e.g., later) stages of CKD, a patient may require input and care from other medical professionals, such as a nephrologist, and may be referred to one when a future eGFR value is estimated for example to be below 30, or above 30 with proteinuria or uncontrolled hypertension. As the eGFR values decrease, these markers may indicate a progression of CKD in which treatment options such as transplants, care, and dialysis are anticipated and appointments with the appropriate medical professional may be scheduled based on future estimated dates according to the estimated eGFR values along the trendline 325. In some embodiments, the future estimated eGFR values may provide immediate interventional treatment options for the patient, e.g., immediate treatments and/or medications that may alter CKD progression. By proactively addressing the progression of CKD, a patient may receive the appropriate treatment without delay or other disruptions, which may allow for an improvement in the patient's treatment and prognosis, and perhaps in some instances a change in the CKD progression timeline.

In some embodiments, the integrated care system, may use the chart 100 to determine when to send alerts to appropriate medical professionals of an upcoming date when a clinical intervention may be necessary. As described above, the integrated care system may be wirelessly connectable for communication to remote devices or a remote location, including but not limited to a mobile communication device (e.g., computer, laptop, tablet, mobile phone, and the like), doctor's office, hospital, call center, and technical support. In some embodiments, the chart 100 may be automatically provided to the electronic medical records or other outside systems in which data is storable, so that clinicians or other medical professionals may access a visualization of the data for ease and quick use. In some embodiments, the chart 100 may be a portion of a report, generatable by the integrated care system. A patient's electronic medical records may be updated with the forecasted data and dates, and in some embodiments may automatically schedule treatments, medications, or consultations, or schedule appointments for the appropriate treatment, or combinations thereof, based on the one or more markers 140*a*, 140*b*, . . . 140*n*.

Figure 2A:
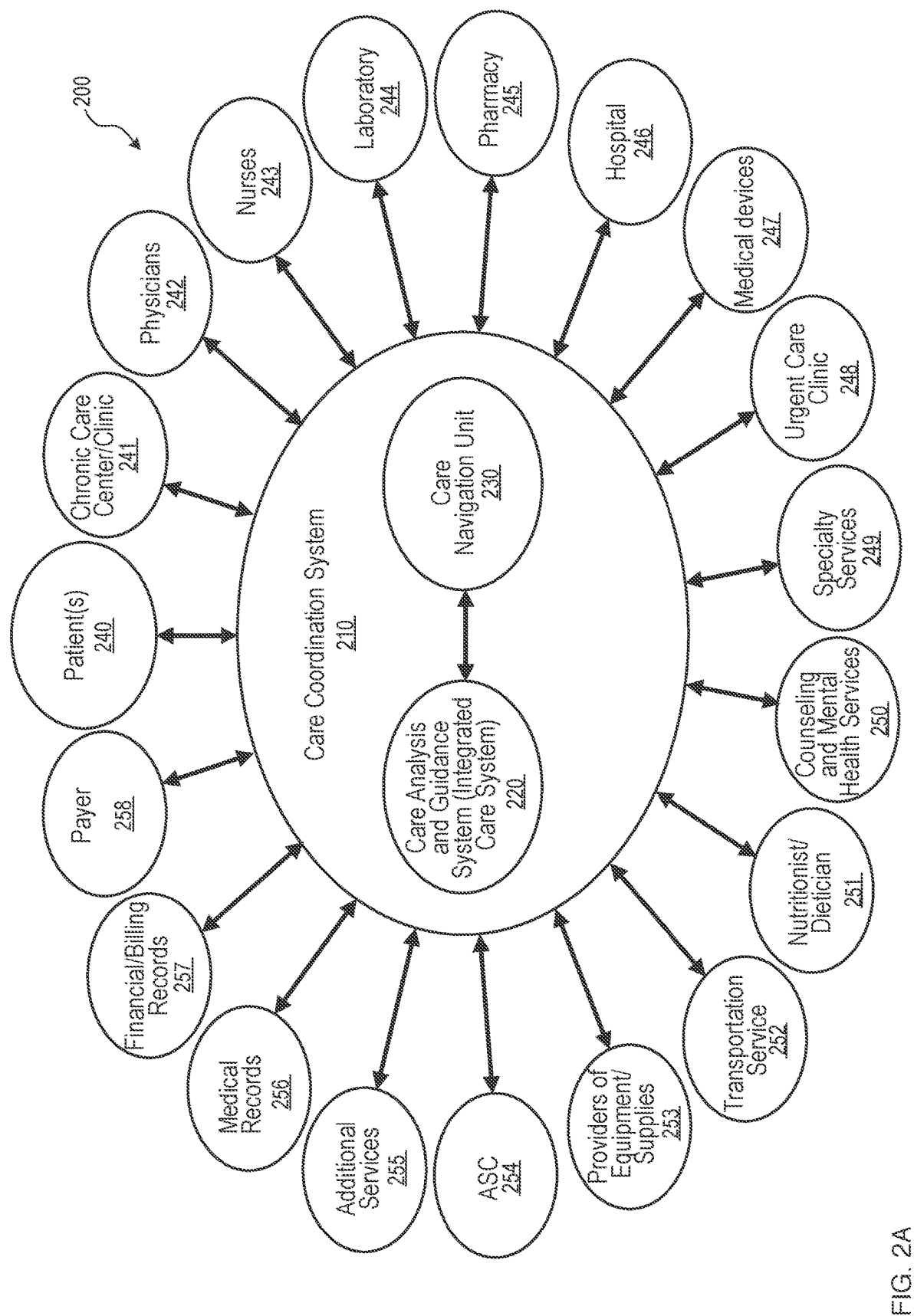
FIG. 2A is a diagram illustrating an exemplary embodiment of a system for providing coordinated healthcare in accordance with the present disclosure.

Referring to FIG. 2A, an example in accordance with the present disclosure includes a coordinated care framework 200 for treating a patient or population of patients 240. The overall care of the patient/population 240 is overseen and coordinated by a care coordination system 210. The care coordination system 210 includes a care analysis and guidance system 220 (which is referred to herein interchangeably as an "integrated care system"), which receives, analyzes, and creates data used to coordinate the care of the patient/population 240. The care coordination system 210 utilizes a care navigation unit (CNU) 230, which implements the coordinated care in accordance with data received from the care analysis and guidance system 220. To manage the overall health and well-being of the patient/population 140, the care coordination system 210 communicates with numerous relevant entities and components. In FIG. 2A, the double-arrow lines graphically represent communication and interaction flows/channels.

In the example illustrated in FIG. 2A, the care coordination system 210 coordinates care for the patients 240 among entities that include chronic care centers or clinics 241, physicians 242 (which may include nephrologists, especially for renal patients), nurses 243, laboratories 244 (e.g., blood labs or other diagnostic labs), pharmacies 245, hospitals 246, medical devices 247 (e.g., dialysis machines or other medical treatment/monitoring devices), urgent care clinics 248, specialty services 249, counseling and mental health services 250, nutritionists/dieticians 251, transportation services 252, providers of medical equipment and supplies 253, ambulatory surgical centers (ASCs) 254, additional services 255, medical records 256, financial and billing records 257, and payer(s) 258 (e.g., CMS or private insurer).

It should be understood that some example embodiments may include other entities not shown, and/or may exclude some of the entities shown. Further, it should be understood that the illustrated communication channels are not exclusive, and the various entities may also, where appropriate, communicate directly or indirectly between each other and/or the patients 240. In some examples, the communication between the care coordination system 210 and one or more of the other entities may be indirect, flowing through one or more intermediary entities. For example, coordination of nurses 243 may be conducted directly between the care coordination system 210 and the nurses 243 or via intermediary channels such as a clinic 241, 248, a hospital 246, or any other suitable channel.

In accordance with some examples, the framework 200 of FIG. 2A may be used in treating diseases such as the progression of kidney disease, e.g., End-Stage Renal Disease (ESRD) and/or Chronic Kidney Disease (CKD). Patients with ESRD are patients undergoing long-term care for kidney disease, e.g., by dialysis treatments. As described above, coordinated care framework 200 may be utilized for obtaining, storing, and generating patient information, including but not limited to electronic medical records, calculated patient parameters, and/or integration with other systems, for interventional treatment options for patients. Monitoring health status trends of dialysis patients may pose challenges. For example, patients may exhibit varying and irregular degrees of functional/cognitive impairment, and may be coupled with complex clinical abnormalities that are independent of a patient's length of time on dialysis. Additionally, in diseases having advancing stages, a patient's condition may change at each medical evaluation. As a patient may interact with several medical professionals (e.g., physician, clinician, nutritionist, nephrologist, mental health professional, and the like), progression of disease may not be known until the patient returns to a particular medical professional. Patient treatments may be inadvertently missed or delayed until visiting the appropriate healthcare provider. In accordance with exemplary embodiments of the present disclosure, coordinated care framework 200, including care analysis and guidance system 120, patient information may be incorporated into coordinated care framework 200 so that disease progression may be monitorable. Additionally, in some embodiments, future patient parameter values may be estimated, based on historic patient parameter values. This may be advantageous for providing proactive and timely interventional treatment to a patient, which may slow or reverse disease progression.

A care analysis and guidance system (integrated care system) 220 may include and execute various healthcare-related models and/or programs. In some examples, these models and/or programs are specifically adapted to implement or carry out particular value-based care frameworks (for example, ESCO models, other ACO models, Chronic Special Needs Plans (C-SNP's), and the like), whereas other examples may include models/programs generally applicable across multiple value-based care frameworks. It is also understood that additional types of value-based care models may be provided for other chronic illnesses, including but not limited to chronic kidney disease, or one or more of the other chronic diseases and conditions mentioned above. These healthcare models may influence improvements in providing value-based care to a patient, for example, by more efficiently managing a patient's care within a specified structure, and may replace conventional fee-for-service (FFS) models. Fee-for-service models may typically focus on volume over the quality of individualized patient care, with little incentive to improve a patient's overall health, which may be less efficient and have lower effectiveness than value-based models.

Shifting patient care away from conventional fee-for-service models to value-based healthcare models may improve care received by patients, reduce total costs, and may improve management of large patient populations diagnosed with the same chronic disease. For example, as mentioned above, value-based healthcare models may pay providers based on a quality of care (e.g., clinical outcomes, meeting specific performance criteria, etc.) received by the patients, and providers and patients may benefit from a focus on addressing and improving the overall health of patients. For example, CMS may set a budget for patient care for a diagnosed illness (e.g., ESRD), thereby incentivizing healthcare providers for innovations to lower costs in providing treatment to the illness. In some embodiments, payments may be associated, or negotiated through "shared risk" contracts, in which the cost, as well as savings, associated with an illness and the coordinated care of a patient is shared by the provider as well as the payer. This arrangement is present in the ESCO model described in greater detail above.

In some embodiments, a care coordination system may identify, test, and/or evaluate innovations through the CEC/ESCO framework for improving patient care to Medicare beneficiaries diagnosed with ESRD. The care coordination system may provide a structure for dialysis clinics, nephrologists or other specialists, and/or other providers to be connected to each other for care coordination for aligned beneficiaries. Value-based healthcare models may incentivize providers based on a quality of care of services delivered. For example, the care coordination system may incorporate incentives for improved care coordination, individualized patient care, and/or improved long-term health outcomes of a patient population. The care coordination system may also coordinate outcomes, e.g., clinical quality, financial, etc., measured by Medicare Part A (e.g., hospital insurance) and B (e.g., medical insurance) spending, including spending related to dialysis services for their aligned ESRD beneficiaries. It is understood that some value-based healthcare models may also include Medicare Part D (e.g., prescription drug coverage) spending.

An integrated care system 220 may form a part of a clinical system for diagnosing and treating a patient in all aspects of care. The integrated care system 220 may be connectable to additional clinical systems, including but not limited to a pharmacy, a CKD/ESRD data registry, and the like. For example, the integrated care system may automatically send prescriptions and other patient information to a pharmacy based on information provided by a medical professional, and may be able to send and receive data and information to the CKD/ESRD data registry, for comparison to other patients and projections for future treatment. The integrated care system may determine events associated with CKD/ESRD and take appropriate action, including but not limited to informing patients, informing clinicians of when specific interventions are warranted, and/or alerting clinicians to upcoming important dates for interventions.

One or more outside, or external, systems may also be connectable to the integrated care system 220. For example, the external systems may include one or more of diagnostic and/or treatment equipment such as a dialysis machine, labs, doctor's office, hospital, and/or electronic medical records.

Patient information may be sent and received between the integrated care system and the external systems, so that patient care may be more efficient, standardized, and consistent across several functions. For example, the integrated care system 220 (see FIG. 2A) may receive information from a patient's electronic medical records, thereby accessing historical information. A dialysis unit, or dialysis machine, doctor's office, labs, and hospitals may send and receive information to and from the integrated care system based on patient treatment.

As described below with respect to FIGS. 12-15, in some embodiments, a care coordination system may provide information to a dialysis machine 1200, 1300, 1400, for use in dialysis treatment. In some embodiments, the integrated care system may send the dialysis machine 1200, 1300, 1400, a prescription from a medical professional for a prescribed dialysis treatment, in which case the integrated care system may receive the prescription from a doctor's office or hospital. The integrated care system may also be able to verify the prescribed treatment against the patient's lab work or medical records, and in some instances may remotely program the prescription onto the patient's dialysis machine, or forward the prescription to the machine for local set-up. In this manner, the patient may be sure to receive the necessary and correct treatment and may be prevented from administering or receiving an improper amount of dialysis treatment, thereby reducing human error and improving patient care. The integrated care system 220 may also be able to inform the relevant medical professional based on information received from these external systems, as well as the additional clinical systems, e.g., to provide appropriate medical treatment to the patient.

Figure 2B:
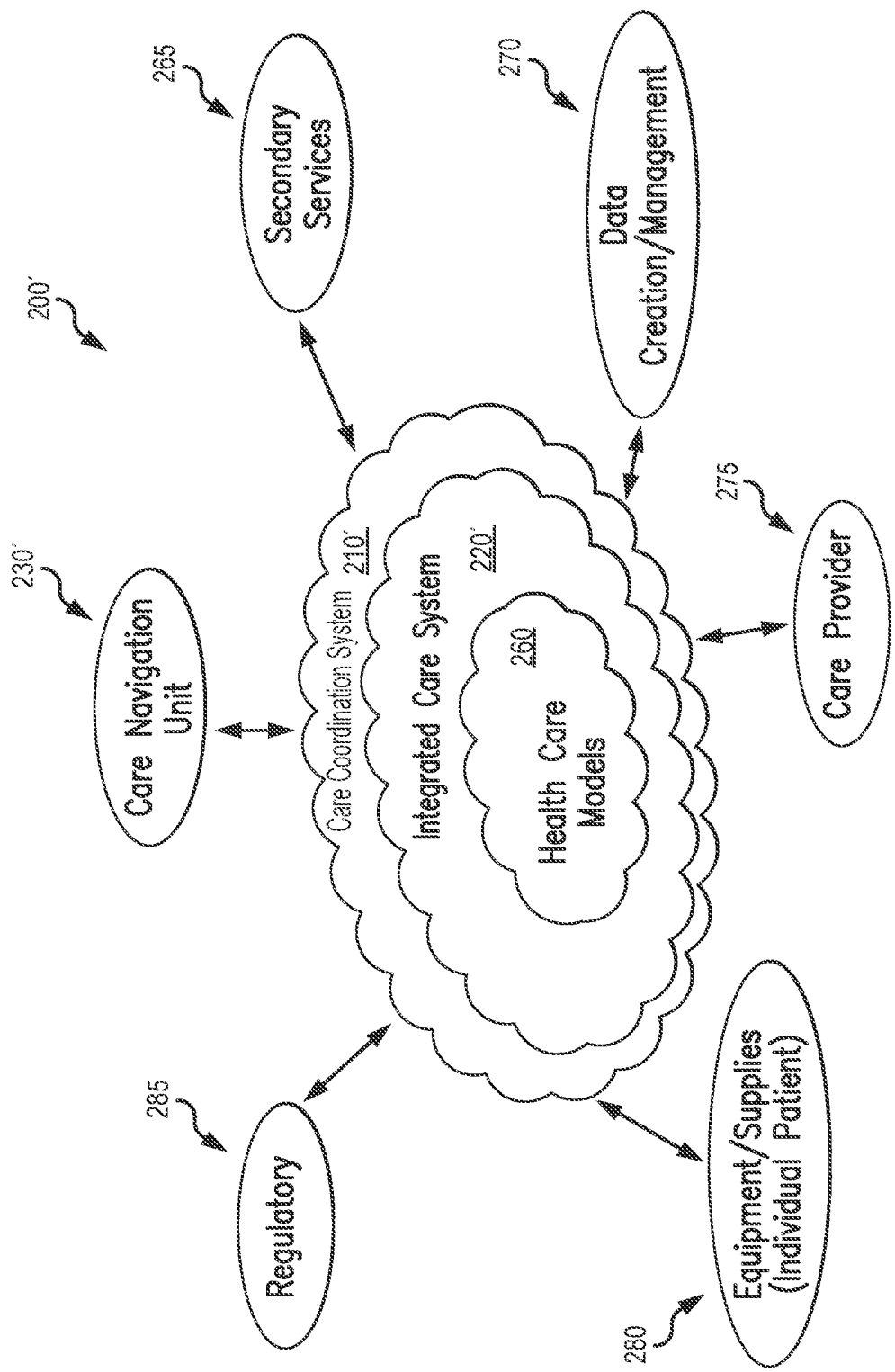
FIG. 2B is a diagram illustrating an exemplary embodiment of systems for assessing and treating disease, including kidney disease, in accordance with the present disclosure.

FIG. 2B is another illustration of a care coordination framework. Coordinated care framework 200' of FIG. 2B shares the features described herein with respect to coordinated care framework 200 of FIG. 2A except to the extent described otherwise. The coordinated care framework 200' described in this example is provided for integrating patient care in treating kidney disease, e.g., ESRD and/or CKD is shown (although it may be adapted as well for other chronic conditions similar to the framework of FIG. 2A). A care coordination system 210' may coordinate at least some aspects of a patient's care with the integrated care system 220' (which may include and execute healthcare-related models and/or programs 260), to support patient care. Various components may engage within the care coordination system 210' to provide complete patient care via the care framework. For example, any number of integrated care components may send and receive information to and from the integrated care system 220', including but not limited to a secondary services component 265, data creation and/or management component 270, care provider component 275, equipment and/or supplies component 280, and regulatory component 285. In some embodiments, the care coordination system 210' may engage with third party resources, including but not limited to lab services, research, etc. In some embodiments, the care framework may encompass, or is implemented by, or is associated with, a care navigation unit 230'. In the example of FIG. 2B, it is noted that the care navigation unit 230' is indicated as a separate entity from the care coordination system 210', but it should be understood that in other examples (see, e.g., FIG. 2A), the care navigation unit may be included as part of the care coordination system.

Figure 6:
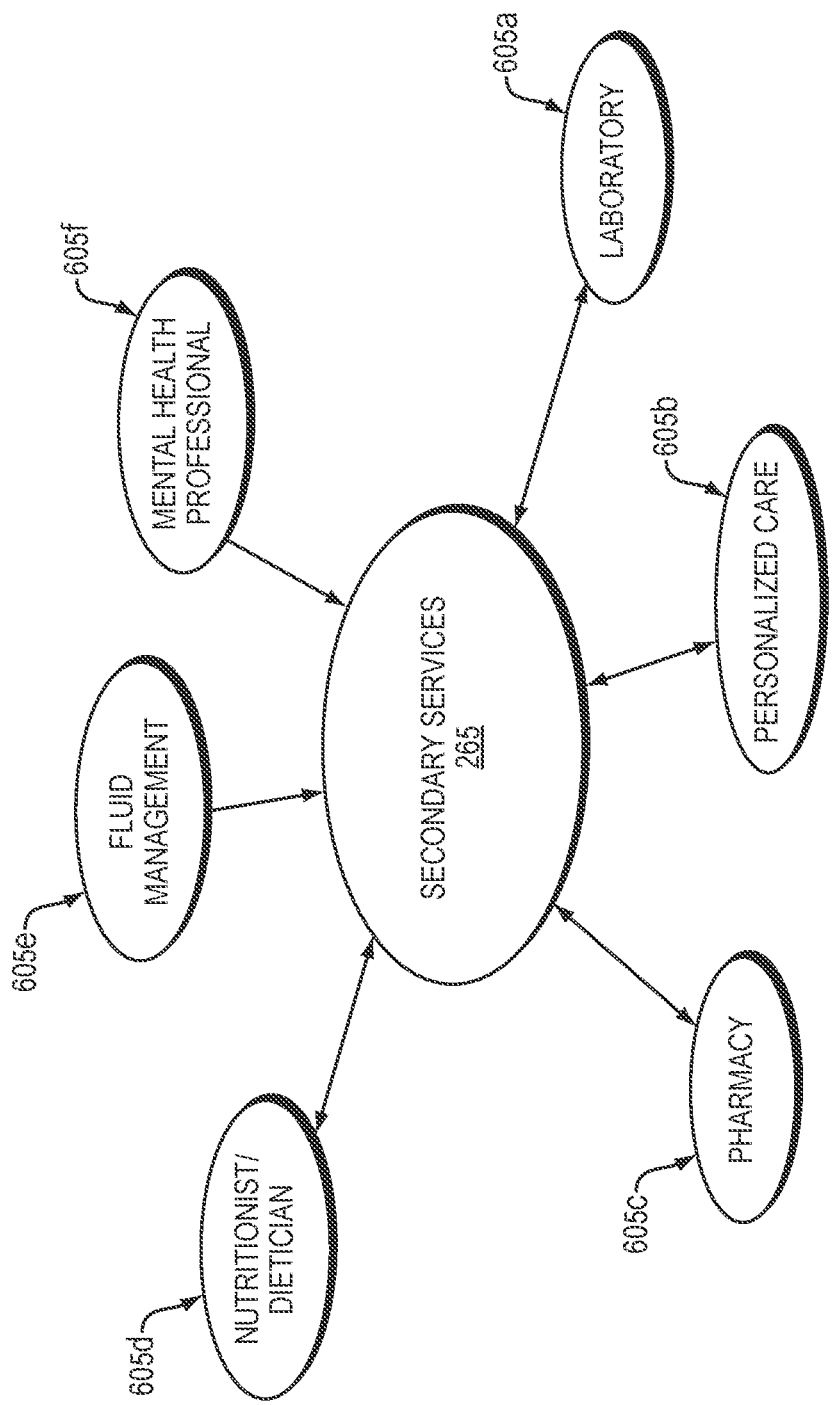
FIGS. 6-10 are diagrams illustrating exemplary embodiments of components of systems for providing coordinated healthcare, in accordance with the present disclosure.

Each component of an integrated care system (e.g., care analysis and guidance system) 220, 220' may include one or more units, including internal services and support as well as external services and support, as described above. As shown in FIG. 6, the secondary services component 265 may include any number "n" of services 605a, 605b, . . . 605n related to secondary patient services. For example, secondary services may include laboratory 605a, personalized care 605b, and/or pharmacy 605c. Each of the secondary services 605a, 605b, . . . 605n may send and receive patient information to the integrated care system 220, 220', for compilation and analysis. For example, a laboratory may automatically send results of patient bloodwork and other test results to the integrated care system 220, 220'. Additionally, the integrated care system 220, 220' may automatically send testing instructions to the laboratory for selected tests on patient samples, based on determinations from medical professionals, and/or other information gathered by the care coordination system 210' via a care framework. Similarly, the integrated care system 220, 220' may automatically send prescriptions and dosage instructions to a pharmacy based on a patient's test results and other factors determined by the integrated care system 220, 220'. The pharmacy may also send information to the integrated care system 220, 220' related to other patient prescriptions for potential adverse drug interactions, how timely a prescription is refilled, and/or patient interaction with the pharmacist, etc.

In some embodiments, a patient may benefit from care by a nutritionist and/or dietician 605d, to adjust to dietary restrictions as a component to their care. For example, ESRD patients may have prescribed dietary requirements are part of receiving hemodialysis and other treatment for their kidney disease. A patient may benefit from consultation with a nutritionist and/or dietician, for moving towards a healthier eating lifestyle and other potential health-related benefits. Fluid management 605e may also be managed for a patient, to ensure a patient is receiving proper amounts and types of fluid. Patients living with CKD and/or ESRD may have fluid restrictions for better dialysis outcomes. Some patients may have difficulty in understanding liquid intake, and/or may be unable to reliably track their fluid intake. In some embodiments, fluid management may be managed by a nutritionist and/or dietician, although it is understood that in other embodiments a patient's fluid intake may be managed by another medical professional. In embodiments, a patient may benefit from care by mental health professionals 605f, for example, psychologists, psychiatrists, and/or other counseling services. As described above, a patient's mental well-being may be affected by progression of an illness, and may otherwise be missed by other medical professionals in the course of treatment. As such, scheduling and providing access to mental health professionals may improve the patient's total health.

Figure 7:
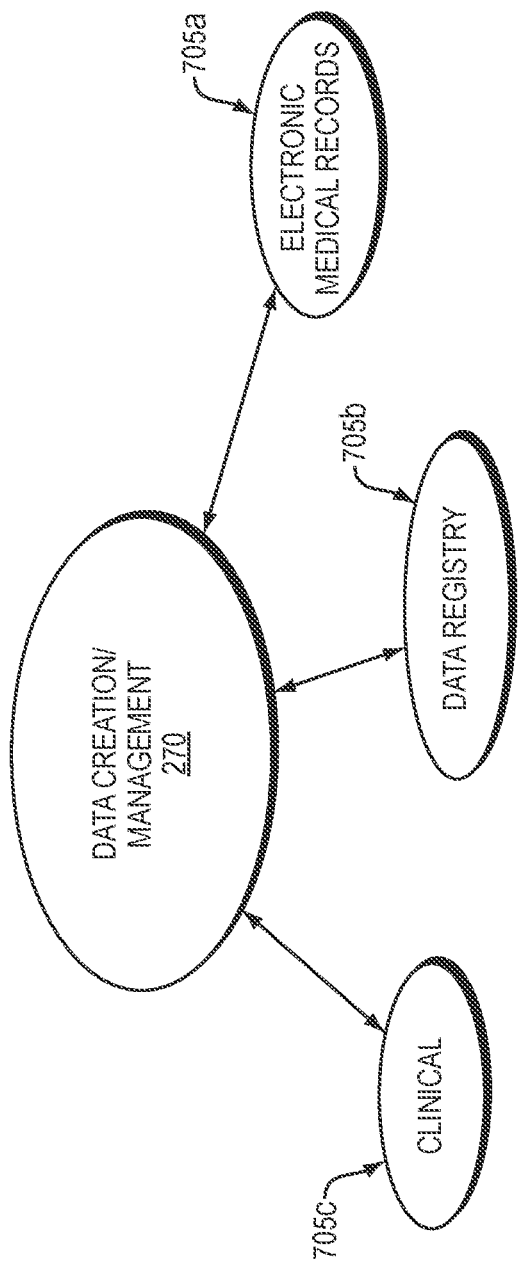

Referring now to FIG. 7, the data creation/management component 270 may include one or more units related to the creation and/or management of patient data, including internal services and support as well as external services and support, as described above. For example, the data creation/management component 270 may include any number "n" of services 705a, 705b, . . . 705n. As shown in FIG. 7, electronic medical records (EMR) 705a, data registry 705b, and clinical information 705c, may receive, store, and/or send patient data records as determined by the care analysis and guidance system 220, 220'. For example, a patient's medical records may be automatically updated after receiving lab results, treatment information, and/or notes from medical professionals. The care analysis and guidance system 220, 220' may utilize a patient's medical records for trends or triggering events, so that the care coordination system 210' may provide relevant information to a medical professional for treatment and other care option recommendations and timing and coordination of various types of possible interventions. In some embodiments, the care analysis and guidance system 220, 220' may analyze multiple patients as part of a data registry, for determining global trends and analyzing data from a macro-level.

Figure 8:
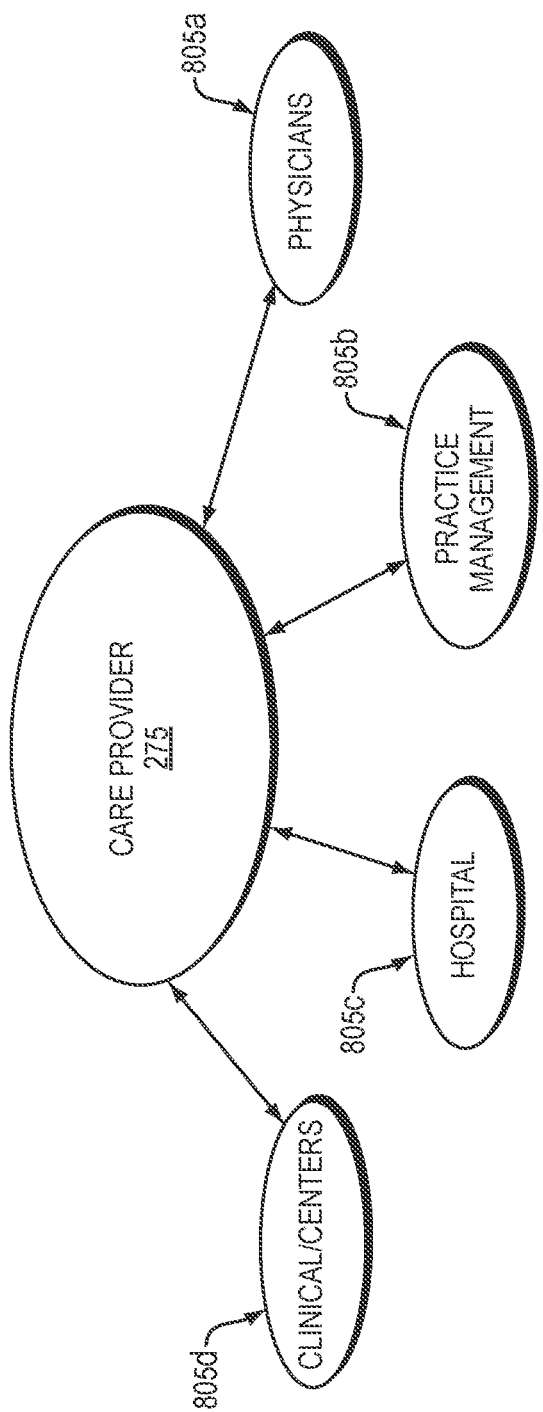

FIG. 8 shows an exemplary care provider component 275, including one or more units which provide patient care, as indicated by reference numerals 805a, 805b, . . . 805n. Any number "n" of units may be included in the provider component 275. In some embodiments, care providers may include physicians and/or physician groups 805a (e.g., primary care physicians (PCP) and specialists such as nephrologists), practice management systems 805b, hospitals 805c, and/or clinic/centers 805d, although additional or alternative care providers may also be envisioned. The integrated care system 220, 220' may send and receive information to and from the care providers for patient treatment. For example, the integrated care system 220, 220' may receive physician notes of patient examinations, hospitalization information, and the like, and may send calculated information and other determined factors based on other patient data received. For example, the integrated care system 220, 220' may send estimations and treatment recommendations to identify, reduce, avoid, and/or eliminate patient risk of aspects and/or effects of renal disease or renal disease treatments for providing treatment to a patient based on all received patient data and assessments performed thereon.

Figure 9:
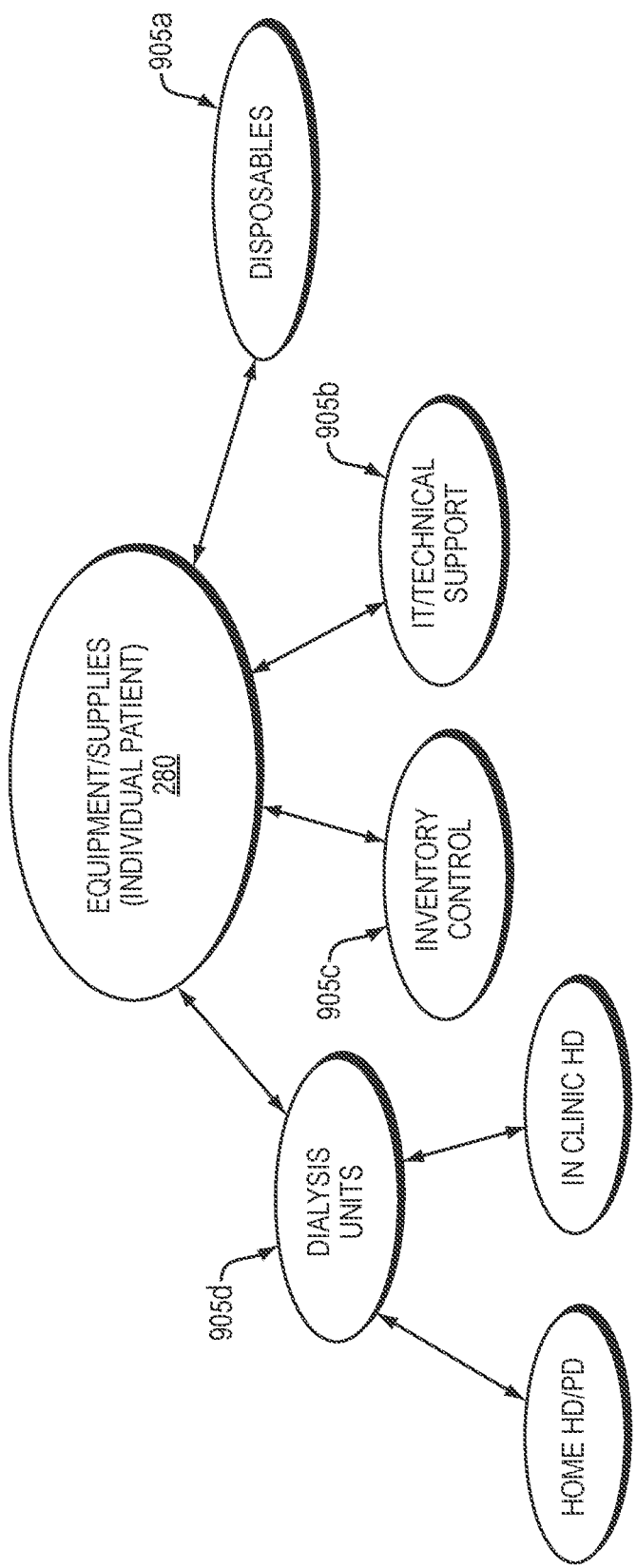

FIG. 9 shows an exemplary equipment and/or supplies component 280, for example, treatment supplies, for an individual patient, which may include any number "n" of services 905a, 905b, . . . 905n. In some embodiments, the integrated care system 220' may send and receive information related to disposable medical equipment 905a, information technology (IT) technical support 905b, inventory control 905c, and/or dialysis units 905d. As described above, many patients receive treatment at home, such as home dialysis, requiring an ongoing supply of disposable medical supplies for each treatment. Deliveries of supplies and/or dialysis equipment may be automatically monitored, replenished, and/or inventoried by the integrated care system 220, 220', to ensure proper machine functioning and a steady supply of materials and resources to ensure a patient receives all prescribed treatments.

Figure 10:
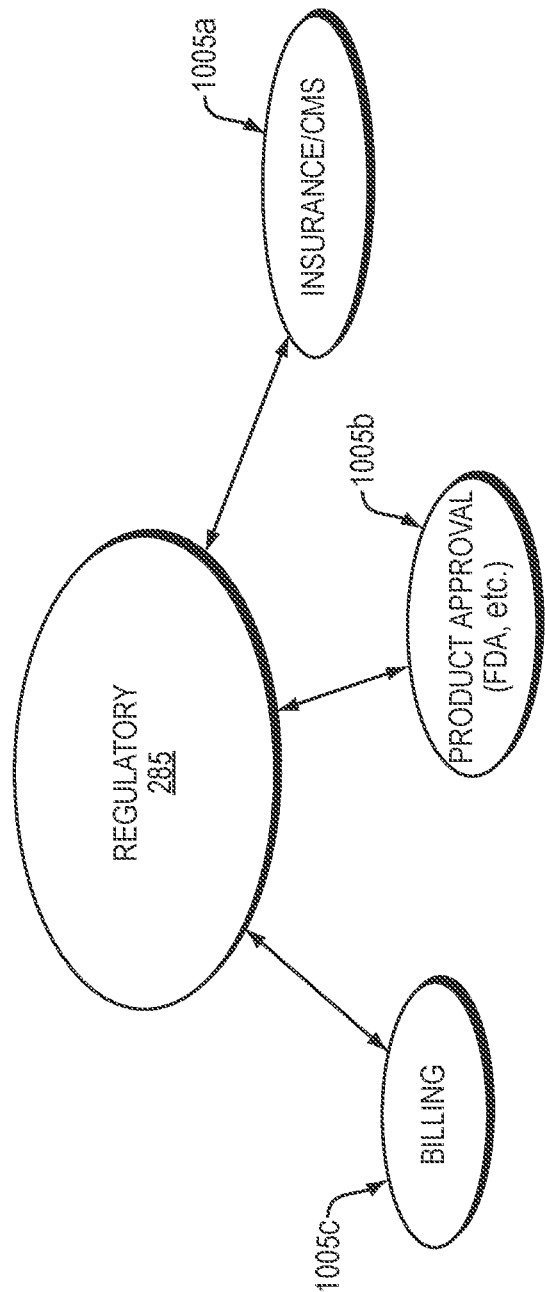

FIG. 10 shows an exemplary regulatory component 285, which may include any number "n" of services 1005a, 1005b, . . . 1005n related to governmental and regulatory requirements. For example, certain state and federal regulations and regulatory authorities may be involved in insurance and/or Centers for Medicaid and Medicare Services (CMS) 1005a, product approvals for the public (e.g., the Food and Drug Administration (FDA)) 1005b, and billing 1005c. The integrated care system 220, 220' may send and receive information to and from each of these units to ensure correct billing coding, regulatory approvals, and/or insurance payments.

Figure 11:
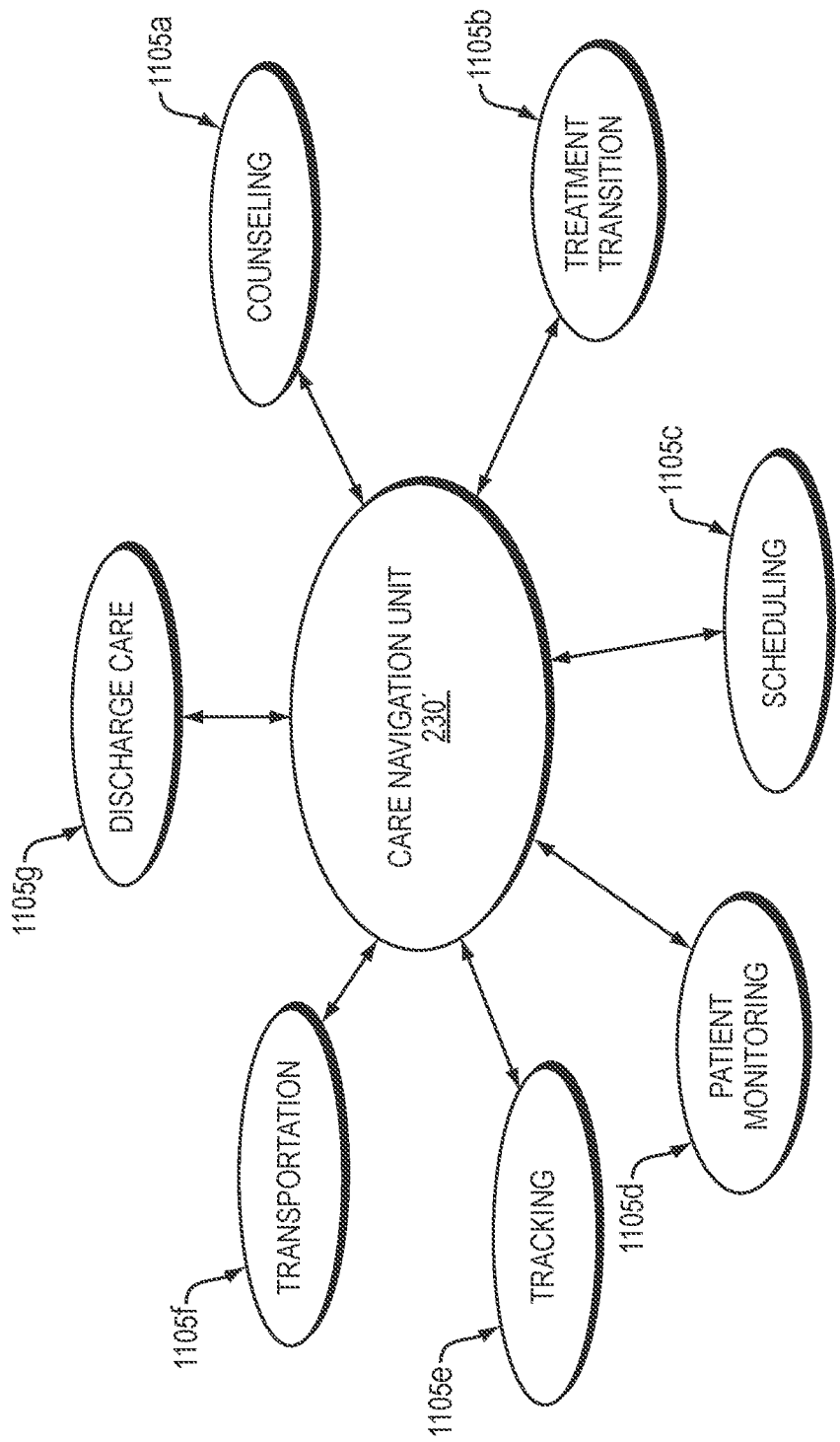
FIG. 11 is a diagram illustrating exemplary embodiments of care coordination components of systems providing coordinated healthcare, in accordance with the present disclosure.

A care navigation unit 230, 230', as introduced above, may oversee and coordinate patient care based on analysis and calculations by the integrated care system 220, 220' determined from data and information from any of the components 265, 270, 275, 280, 285, as well as the care coordination system 210'. For example, a care navigation unit 230', may coordinate care to patients to follow through on interventional treatments to address functional and/or cognitive patient impairment over time, improve comorbidity management, and help drive high-value care options and timing of treatment decisions to patients over time. As shown in FIG. 11, care navigation unit 230, 230' may include different aspects of health care coordination as indicated by reference numerals 1105a, 1105b, . . . 1105n, including but not limited to counseling, treatment transition, scheduling, patient monitoring, tracking, transportation, and/or discharge care. For example, the integrated care system 220, 220' may determine that a patient requires transportation to/from a treatment center, and may automatically schedule transportation, e.g., public transportation, carpool, taxi, ride share, etc., so that the patient may not miss a scheduled treatment. Additionally, the integrated care system 220, 220' may send patient results to the relevant care providers, e.g., medical specialists, doctors, and/or nurses, for monitoring and/or treatment recommendations. Care navigation unit 230' may provide services to patients addressing their complete healthcare needs related to their kidney disease.

The care navigation unit 230' may include treatment transition 1105b, for an integrated care system 220, 220' to coordinate patient care through progression of kidney disease. For example, a patient may initially be diagnosed with chronic kidney disease (CKD). Over time however, without interventional treatment (e.g., a kidney transplant) or improved kidney function, the patient may progress to end-stage renal disease (ESRD). As the patient's kidney disease progresses, the patient may need additional services, support, and/or health care, which may be overseen and/or managed under the care framework 200' by the care navigation unit 230' via the integrated care system 220, 220' and through a care framework of care coordination system 210'. By calculating estimated future values of one or more patient parameters, a patient's disease progression may be trackable, for proactively addressing and treating conditions. For example, the care navigation unit 230' may coordinate specified patient treatments, and scheduled appropriately, so the patient is unlikely to miss a treatment, or have complications from an unknown progression of disease.

Figure 3:
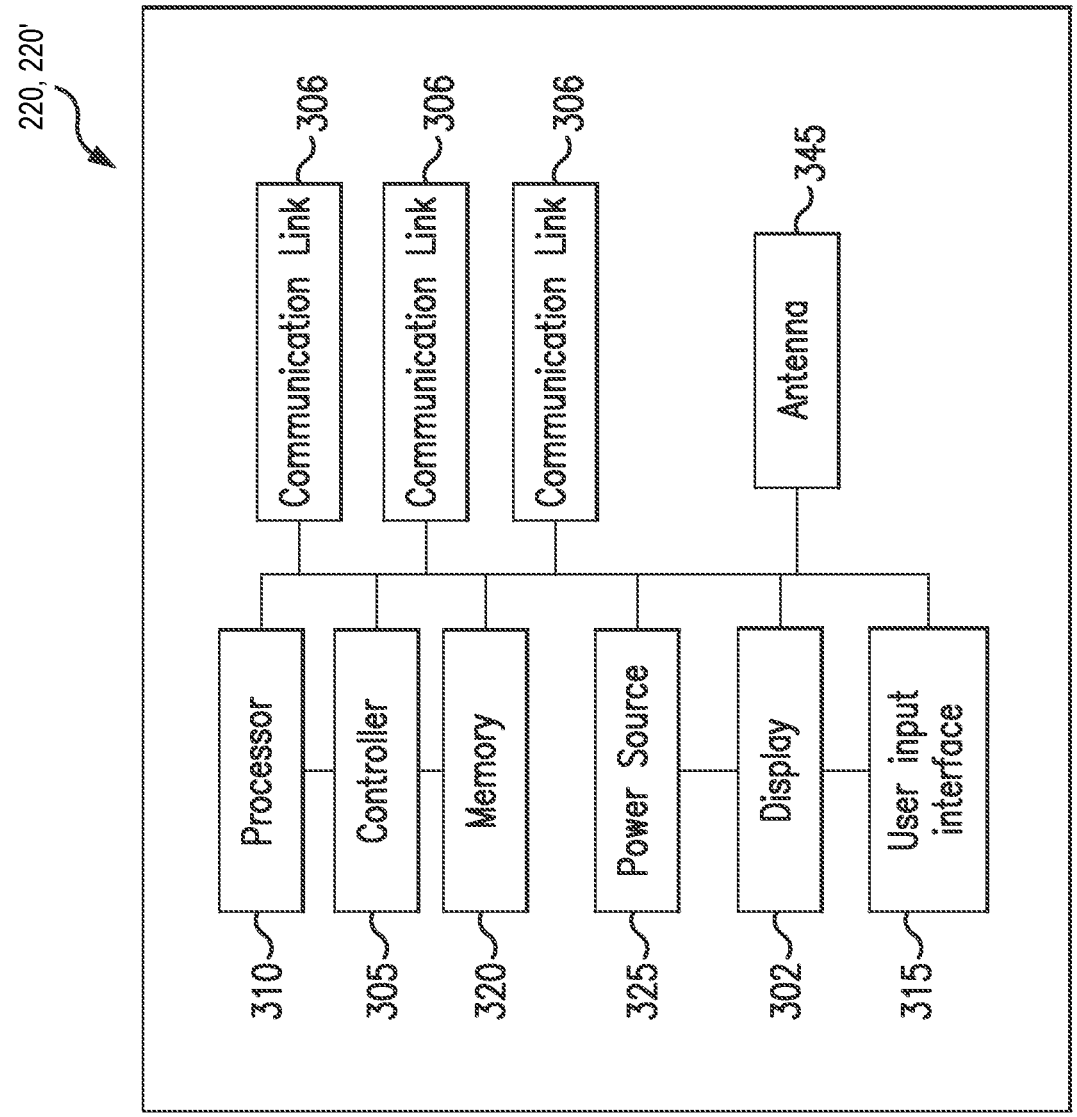
FIG. 3 is a block diagram illustrating an exemplary embodiment of an integrated care system in accordance with the present disclosure.

Referring now to FIG. 3, an integrated care system, such as integrated care system 220, 220', may include a controller 305, a processor 310, and a memory 320. The controller 305 may automatically control signals received and sent to other systems, e.g., the additional clinical systems, the external systems, and the practice management and billing system. Communication between the controller 305 and other systems may be bi-directional, whereby the systems may acknowledge control signals, and/or may provide information associated with the system and/or requested operations. Additionally, a user input interface 315 and display 302 may be disposed to receive and/or display input from a user, e.g., a patient or a medical professional such as a doctor, nurse, technician, or the like. Examples of the components that may be employed within the user input interface 315 include keypads, buttons, microphones, touch screens, gesture recognition devices, display screens, and speakers. In some embodiments, the integrated care system 220, 220' may be a server, a computer, or other device for storing and processing data, and controlling signals to other systems. A power source 325 may allow the integrated care system 220, 220' to receive power, and in some embodiments may be an independent power source.

The processor 310 may be configured to execute an operating system, which may provide platform services to application software, e.g., for operating the integrated care system 220, 220'. These platform services may include inter-process and network communication, file system management and standard database manipulation. One or more of many operating systems may be used, and examples are not limited to any particular operating system or operating system characteristic. In some examples, the processor 310 may be configured to execute a real-time operating system (RTOS), such as RTLinux, or a non-real time operating system, such as BSD or GNU/Linux. According to a variety of examples, the processor 310 may be a commercially available processor such as a processor manufactured by INTEL, AMD, MOTOROLA, and FREESCALE. However, the processor 310 may be any type of processor, multiprocessor or controller, whether commercially available or specially manufactured. For instance, according to one example, the processor 310 may include an MPC823 microprocessor manufactured by MOTOROLA.

The memory 320 may include a computer readable and writeable nonvolatile data storage medium configured to store non-transitory instructions and data. In addition, the memory 320 may include a processor memory that stores data during operation of the processor 310. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 320 may include executable programs or other code that may be executed by the processor 310. The instructions may be persistently stored as encoded signals, and the instructions may cause the processor 310 to perform the functions described herein. The memory 320 may include information that is recorded, on or in, the medium, and this information may be processed by the processor 310 during execution of instructions. The memory 320 may also include, for example, data records, timing for treatment and/or operations, historic information, statistical information, and informational databases for treatments. A database may be stored in the memory 320 of the integrated care system 220, 220', and may be accessible by the processor 310 and controller 305. For example, historical data of patient information may be extracted from various databases in the integrated system 220, 220', including but not limited to patient lab results, treatment data, technician data during treatment (nurse notes), etc.

The integrated care system 220, 220' may include communication links 306, so that other systems may be connectable to the integrated care system 220, 220'. For example, additional clinical systems, external systems, and practice management and billing systems, may be connectable to the integrated care system 220, 220' to send and receive data and information associated with providing patient care. In some embodiments, the communication links 306 may be wireless, so that the systems may be remote, or the integrated care system 220, 220' and/or one or more of the systems 265, 270, 275, 280, 285, 230' may reside and operate in a cloud-based architecture.

The integrated care system 220, 220' may also be wirelessly connectable via an antenna 345 for remote communication. For example, the integrated care system 220, 220' may determine one or more patient parameters by the controller 305, processor 310, and/or memory 320, and may access other patient parameters being stored by an outside system, e.g., in electronic medical records stored on a server or database in a location remote from the system or machine, or from labs or hospital information. It may be advantageous for the integrated care system 220, 220' to access other patient parameters that may otherwise be unknown or undeterminable in order to provide a complete care analysis of the patient. As described above, patient data may be sent to and/or accessible by the integrated care system 220, 220'. The controller 305, processor 310, and memory 320 may receive, store, and/or determine relevant demographic and laboratory values, or other data, for calculations. For example, the table 150, may be storable as a database. Historic data and information for generating chart 100 may also be storable as a database (see FIGS. 1A-1B).

Figure 4:
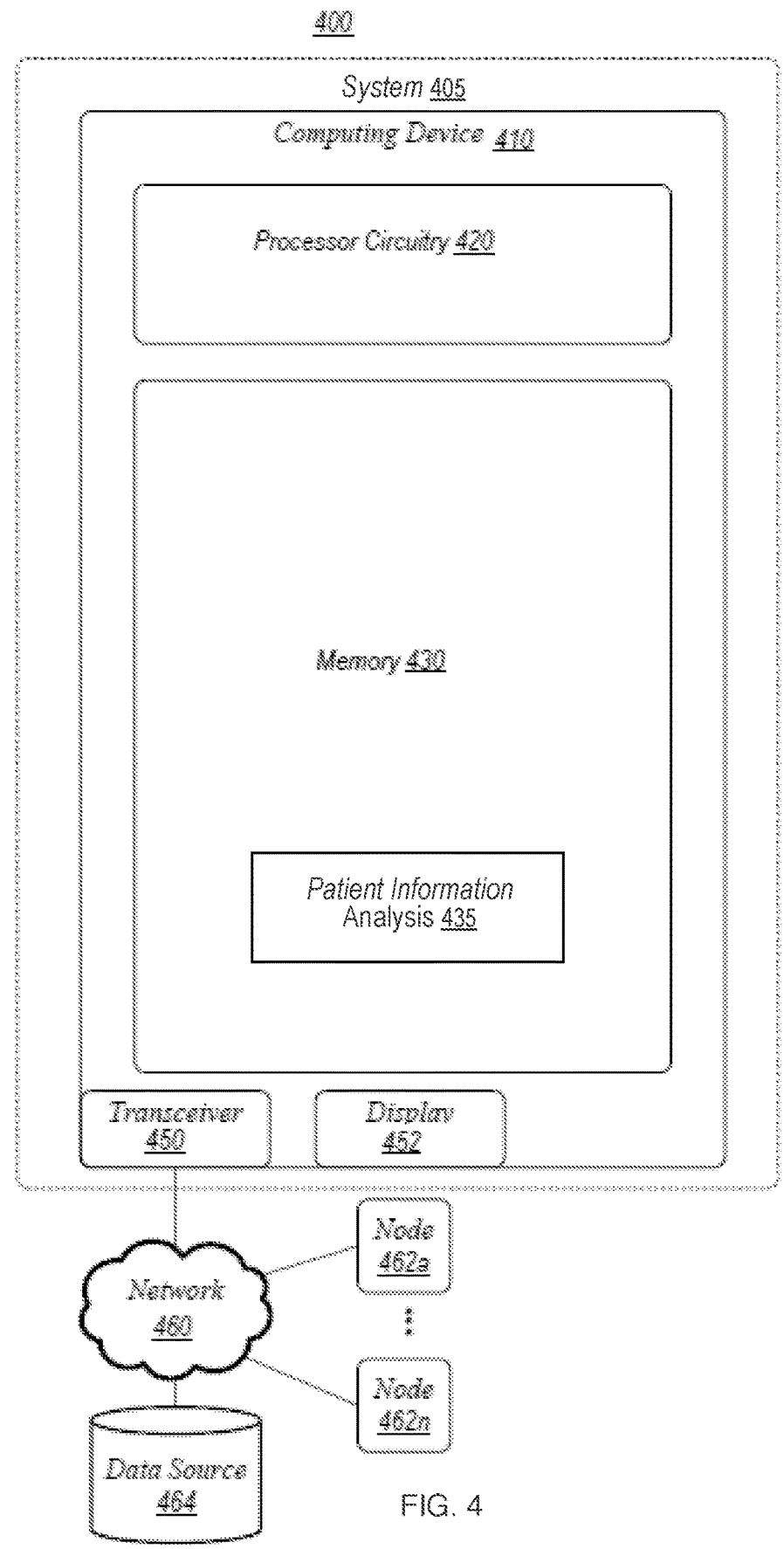
FIG. 4 is a block diagram illustrating an exemplary embodiment of an operating environment in accordance with the present disclosure.
Figure 5:
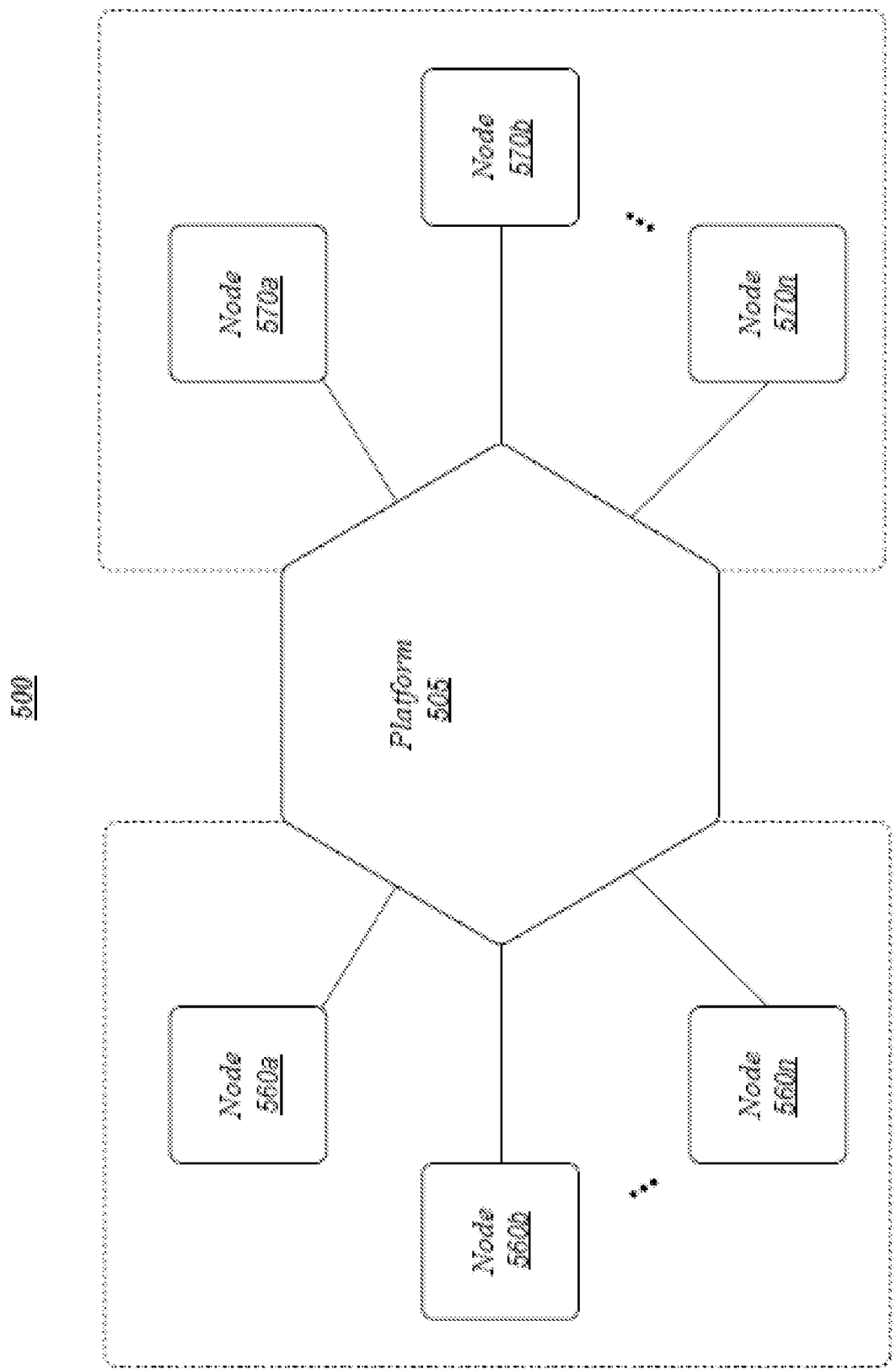
FIG. 5 is a block diagram illustrating an exemplary embodiment of another operating environment in accordance with the present disclosure.

Referring now to FIGS. 4-5, exemplary embodiments of an operating environment for a healthcare system (e.g., coordinated care framework 200, 200'), including integrated care system (care analysis and guidance system) 220, 220', are described. FIG. 4 illustrates an example of an operating environment 400 that may be representative of some embodiments. As shown in FIG. 4, operating environment 400 may include a system 405 operative for treating patients, e.g., patients having chronic illnesses. In various embodiments, the system 405 may include computing device 410. Computing device 410 may include processing circuitry 420, a memory unit 430, a transceiver 450, and/or a display 452. Processing circuitry 420 may be communicatively coupled to memory unit 430, transceiver 450, and/or display 452. It is understood that in some embodiments, system 405 may include the coordinated care framework 200, 200', and in some embodiments, the system 405 may include other systems and/or frameworks.

In some embodiments, computing device 410 may be connected to network 460 through transceiver 450. Network 460 may include nodes 462*a-n*, for example, remote computing devices, data sources 464, and/or the like.

Processing circuitry 420 may include and/or may access various logic for performing processes according to some embodiments. Processing circuitry 120, or portions thereof, may be implemented in hardware, software, or a combination thereof. As used in this application, the terms "logic, "component," "layer," "system," "circuitry," "decoder," "encoder," and/or "module" are intended to refer to a computer-related entity, either hardware, a combination of hardware and software, software, or software in execution, examples of which are provided by the exemplary computing architecture 1500 of FIG. 15. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

It is also understood that components of the processing circuitry 420 may be located within an accelerator, a processor core, an interface, an individual processor die, implemented entirely as a software application and/or the like.

Memory unit 430 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 430 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 430 may store various information, e.g., one or more programs, to perform various functions identifying and treating patients with CKD and/or ESRD. In some embodiments, the memory 430 may include logic having application programming interfaces (APIs) and/or graphical user interfaces (GUIs) to read, write, and/or otherwise access information, such as via display 452, web interfaces, mobile application ("mobile applications," "mobile apps," or "apps"), and/or the like. In this manner, in some embodiments, an operator may search, visualize, read, add to, or otherwise access information associated with a patient population for identifying and treating CKD and/or ESRD.

In some embodiments, memory unit 430 may store various information associated with a patient population for identifying and treating CKD and/or ESRD. In some embodiments, information stored in memory unit 430 may be retrieved from and/or moved into a data source 464 including, without limitation, a hospital information management system (HIMS), laboratory information management system (LIMS), Health Information System (HIS), electronic medical records (EMR), a clinical trial database, and/or the like. In some embodiments, patient information analysis 435, which may be one or more programs, algorithms, or combinations thereof, for identifying and/or treating chronic illness, such as kidney disease, may be implemented.

FIG. 5 illustrates an example of an operating environment 500 that may be representative of some embodiments. As shown in FIG. 5, operating environment 500 may include a platform 505, e.g., a healthcare exchange platform. In some embodiments, the platform 505 may be operative to provide for the exchange of clinical data and/or clinical trial information among interested entities. In various embodiments, the platform 505 may include an application platform operative for identifying a patient population and treating CKD and/or ESRD with services among nodes 560a-n and 570a-n. In exemplary embodiments, the platform 505 may be a software platform, suite, set of protocols, and/or the like provided to customers by a manufacturer and/or developer ("developer") associated with medical devices, medical care services, clinical research services, laboratory services, clinical trial services, and/or the like.

For example, a developer may provide the platform 505 as a data exchange interface for use by various entities, including government entities (for example, the FDA), and other stakeholders (for instance, pharmaceutical manufacturers, medical device manufacturers, and/or the like). An entity, such as a hospital, dialysis clinic, healthcare provider, government entity, regulatory entity, pharmaceutical manufacturer, medical device manufacturer, and/or the like providing and/or receiving clinical trial services via a node 570a-n provided by developer may use the platform 505 to implement processes according to some embodiments. Other entities, may access the platform 505 via a GUI, such as a client application, web interface, mobile app, and/or the like, e.g., for performing functions associated with the memory 522. In some embodiments, at least a portion of the platform 505 may be hosted in a cloud computing environment.

Nodes 570a-n may be data producers for the memory 522 and nodes 560a-n may be data consumers of the memory 522. For example, node 570a-n may include entities providing clinical data, model information, and/or the like used by the memory 522 to generate, perform, and/or evaluate a patient population. Nodes 560a-n may include third-party applications, decision makers, analysis processes, regulators, and/or other data consumers that may be interested in the results of generating, performing, and/or evaluating the patient population. An entity may be both a data producer and a data consumer.

For example, node 560a may be care provider (node 560b) to provide treatment to a patient based on analysis of a patient population including medical records, laboratory data, pharmacy, and the like. (node 570a). Data producers 570a-n may provide analytical data, according to permissions, to the platform 505, for example, in the form of records in a HIMS, LIMS, EMR, and/or the like. Data consumers 560a-n may access analytical data, according to permissions, via the platform 505 (for example, through HIMS, LIMS, EMR, and/or the like and/or local copies of such records).

In some embodiments, the platform 505 may operate according to a cloud-based model and/or an "as-a-Service" model. In this manner, the platform 505 may provide for a service that operates as a single, central platform that allows entities to access clinical data, model information, simulation results, and/or the like.

Figure 12:
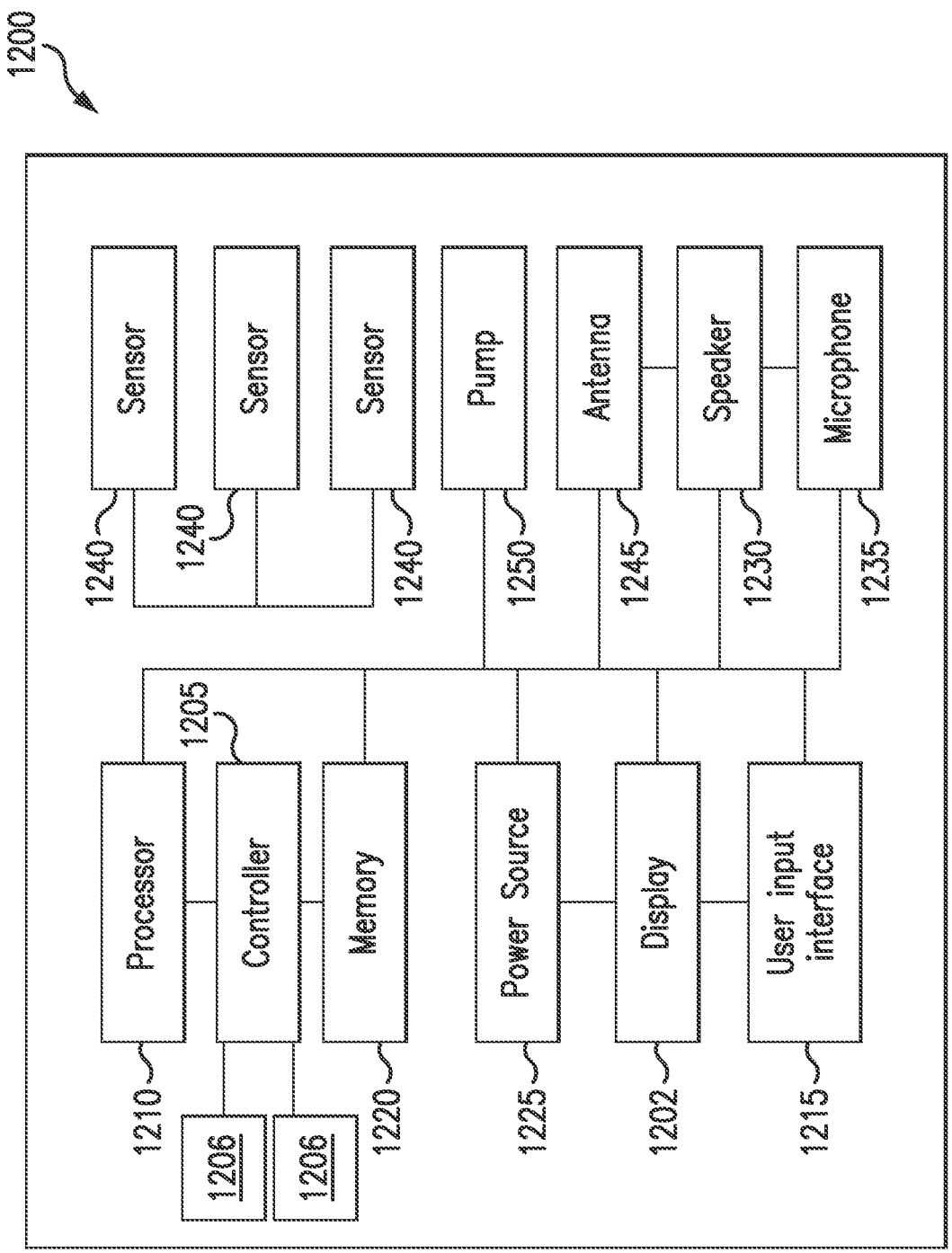
FIG. 12 is a block diagram illustrating an exemplary embodiment of a dialysis machine in accordance with the present disclosure.

In some embodiments, one of the recommended treatments and/or services may be to alter or change a dialysis treatment prescription for a patient. As illustrated in FIGS. 12-14 and described below, a dialysis machine 1200, 1300, 1400, e.g., a dialysis machine such as a peritoneal dialysis machine or a hemodialysis machine, may be connected to the integrated care system 220, 220' for sending and receiving dialysis information to provide appropriate care to a patient. The hemodialysis machine may be located in a renal clinic, such as a kidney care clinic, dialysis clinic, or other third-party care provider. In some embodiments, the peritoneal dialysis machine and/or the hemodialysis machine may be home machines, e.g., treatment may be administered in a patient's home. As described above, an integrated care system may be applicable to other chronic illnesses, and may be connected to machines related to those illnesses, including but not limited to chronic kidney disease, or one or more of the other chronic diseases and conditions mentioned above.

Referring to FIG. 12, a schematic of an exemplary embodiment of a dialysis machine 1200, and a controller 1205 in accordance with the present disclosure are shown. The machine 1200 may be a dialysis machine, e.g., a peritoneal dialysis machine or a hemodialysis machine, for performing a dialysis treatment on a patient (see FIGS. 12-14). The controller 1205 may automatically control execution of a treatment function during a course of dialysis treatment. For example, the controller 1200 may control dialysis treatment based on information received from the care analysis and guidance system 220, 220'. The controller 1205 may be operatively connected to sensors 1240 and deliver one or more signals to execute one or more treatment functions, or a course of treatment associated with various treatment systems. Although FIG. 12 illustrates the components integrated into the dialysis machine 1200, at least one of the controller 1205, processor 1210, and memory 1220 may be configured to be external and wired or wirelessly connected to the dialysis machine 1200, as an individual component of a dialysis system. In some embodiments the controller 1205, processor 1210 and memory 1220 may be remote to the dialysis machine and configured to communicate wirelessly.

In some embodiments, the controller 1205, processor 1210, and memory 1220 of the system or machine 1200, 1300, 1400, may receive signals from sensor 1240 indicating one or more patient parameters. Communication between the controller 1205 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

The dialysis system or machine 1200, 1300, 1400, may also include at least one pump 1250 operatively connected to the controller 1205. The controller 1205 may also be operatively connected to one or more speakers 1230 and one or more microphones 1235 disposed in the system or machine 1200, 1300, 1400. The user input interface 1215 may include a combination of hardware and software components that allow the controller 1205 to communicate with an external entity, such as a patient or other user. These components may be configured to receive information from actions such as physical movement or gestures and verbal intonation. In embodiments, the components of the user input interface 1215 may provide information to external entities. Examples of the components that may be employed within the user input interface 1215 include keypads, buttons, microphones, touch screens, gesture recognition devices, display screens, and speakers.

As shown in FIG. 12, sensors 1240 may be included for detecting and monitoring one or more parameters and be operatively connected to at least the controller 1205, processor 1210, and memory 1220. The processor 1210 may be configured to execute an operating system, which may provide platform services to application software, e.g., for operating the dialysis machine 1200. These platform services may include inter-process and network communication, file system management and standard database manipulation. One or more of many operating systems may be used, and examples are not limited to any particular operating system or operating system characteristic. In some examples, the processor 1210 may be configured to execute a real-time operating system (RTOS), such as RTLinux, or a non-real time operating system, such as BSD or GNU/Linux. According to a variety of examples, the processor 1210 may be a commercially available processor such as a processor manufactured by INTEL, AMD, MOTOROLA, and FREESCALE. However, the processor 1210 may be any type of processor, multiprocessor or controller, whether commercially available or specially manufactured. For instance, according to one example, the processor 1210 may include an MPC823 microprocessor manufactured by MOTOROLA.

The memory 1220 may include a computer readable and writeable nonvolatile data storage medium configured to store non-transitory instructions and data. In addition, the memory 1220 may include a processor memory that stores data during operation of the processor 1210. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 1220 may include executable programs or other code that may be executed by the processor 1210. The instructions may be persistently stored as encoded signals, and the instructions may cause the processor 1210 to perform the functions described herein. The memory 1220 may include information that is recorded, on or in, the medium, and this information may be processed by the processor 1210 during execution of instructions. The memory 1220 may also include, for example, specification of data records for user timing requirements, timing for treatment and/or operations, historic sensor information, and other databases and the like. The medium may, for example, be optical disk, magnetic disk or flash memory, among others, and may be permanently affixed to, or removable from, the controller 1200.

A pressure sensor may be included for monitoring fluid pressure of the system or machine 1200, 1300, 1400, although the sensors 1240 may also include any of a heart rate sensor, a respiration sensor, a temperature sensor, a weight sensor, a video sensor, a thermal imaging sensor, an electroencephalogram sensor, a motion sensor, audio sensor, an accelerometer, or capacitance sensor. It is appreciated that the sensors 1240 may include sensors with varying sampling rates, including wireless sensors. Based on data monitored by the sensors 1240, patient parameters such as a heart rate and a respiration rate may be determined by the controller 1200.

The controller 1205 may be disposed in the machine 1200, 1300, 1400, or may be coupled to the machine 1200, 1300, 1400, via a communication port or wireless communication links, shown schematically as communication element 1206. For example, the communication element 1206 may connect the dialysis machine 1200, 1300, 1400, to the care analysis and guidance system 220, 220', or another remote system such as an outside system or other clinical system. The dialysis machine 1200, 1300, 1400, may be connectable to the integrated care system 220, 220' via the communication element 1206 so that the controller 1205 may send and receive information and other signals to the care analysis and guidance system 220, 220'. As described above, the care analysis and guidance system 220, 220' may direct a prescribed dialysis treatment based on information received from other systems, e.g., outside systems, clinical systems, directly to the dialysis machine to ensure a patient receives the proper treatment. The dialysis machine may also send data and other information to the care analysis and guidance system 220, 220' so that if dialysis treatment requires adjustment, the care analysis and guidance system 220, 220' may ensure any changes will not adversely affect patient health.

As a component disposed within the machine 1200, 1300, 1400, the controller 1205 may be operatively connected to any one or more of the sensors 1240, pump 1250, pump heads 1404, 1406, and the like. The controller 1205 may communicate control signals or triggering voltages to the components of the system or machine 1200, 1300, 1400. As discussed, exemplary embodiments of the controller 1205 may include wireless communication interfaces. The controller 1205 may detect remote devices to determine if any remote sensors are available to augment any sensor data being used to evaluate the patient.

Figure 13A:
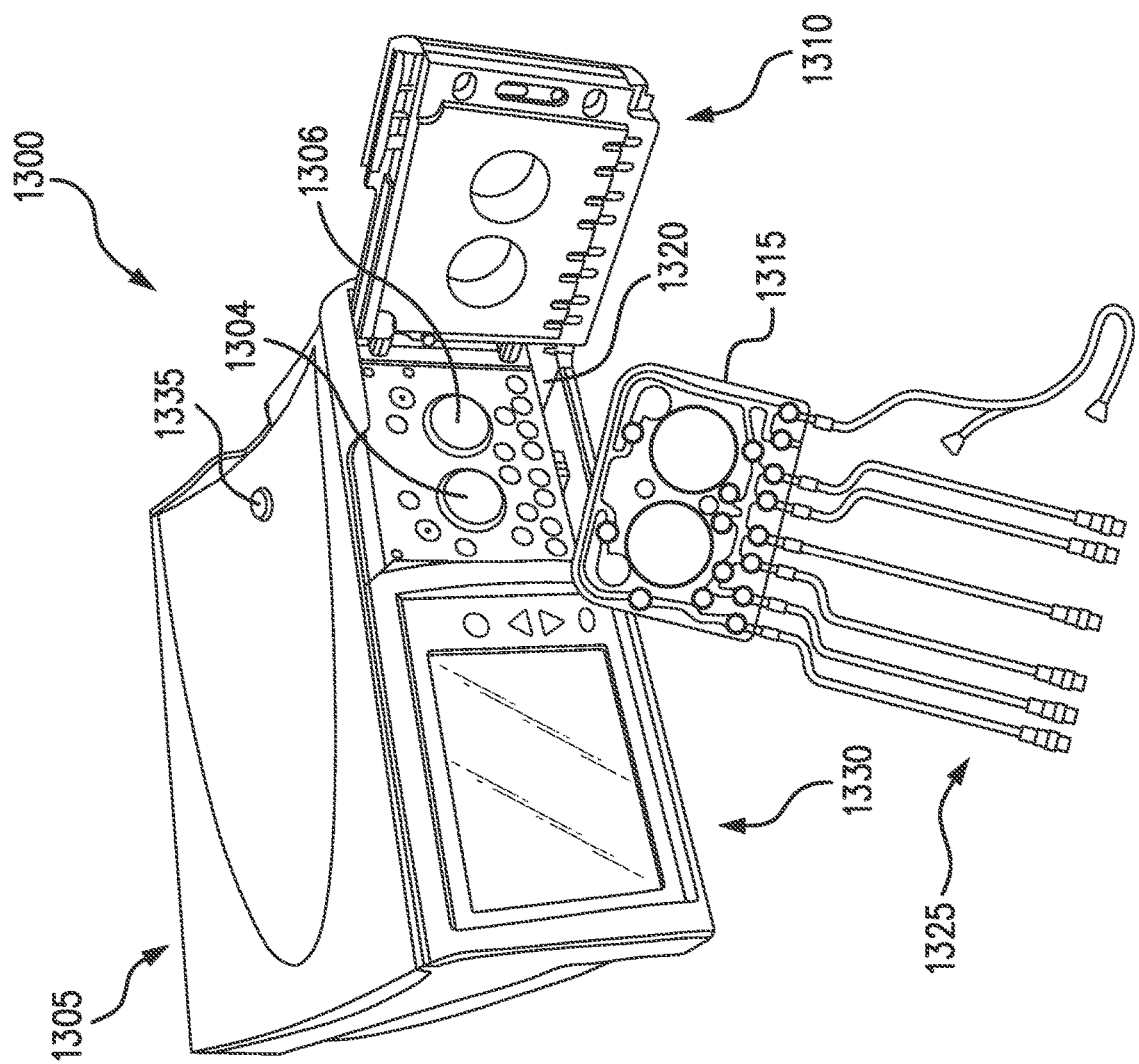
FIGS. 13A-13B illustrate an exemplary embodiment of a dialysis system in accordance with the present disclosure.
Figure 13B:
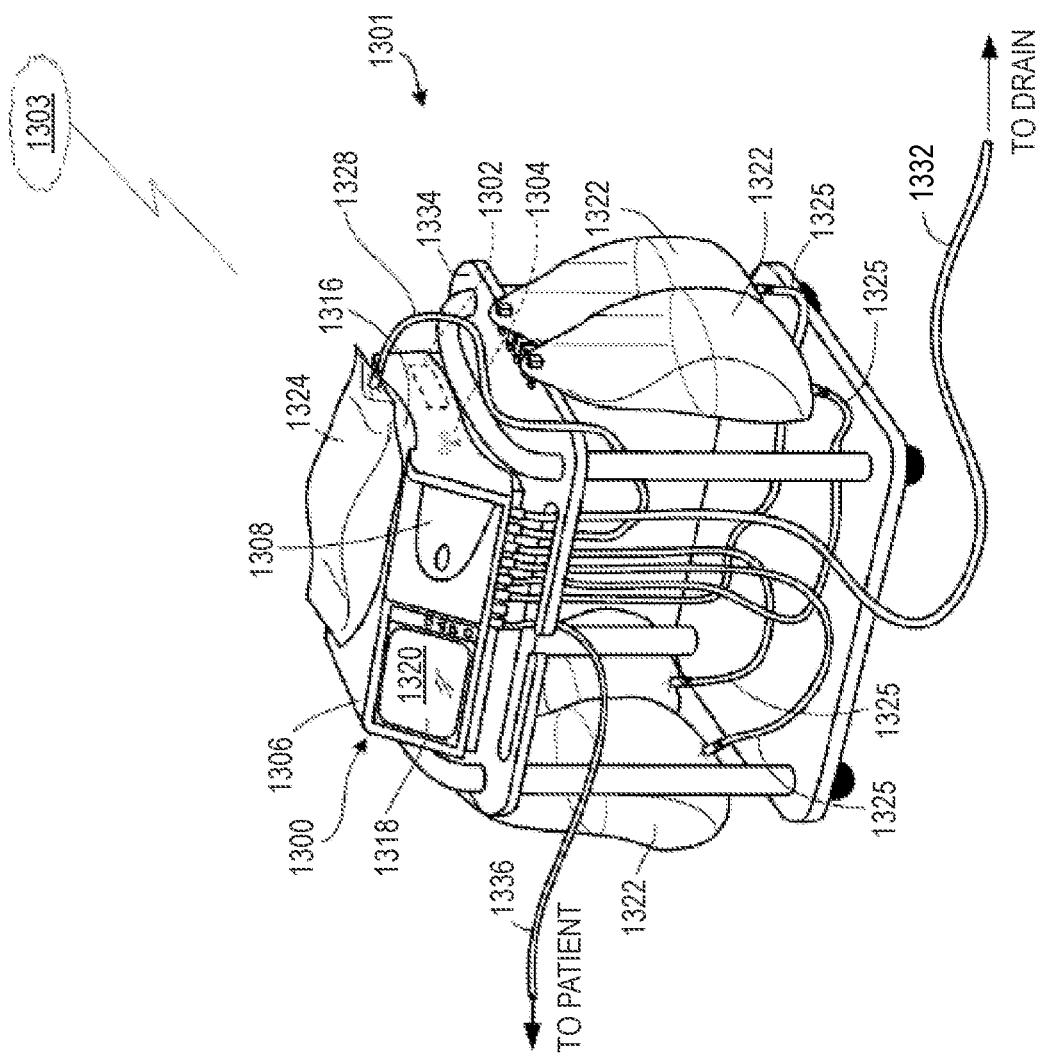
Figure 14:
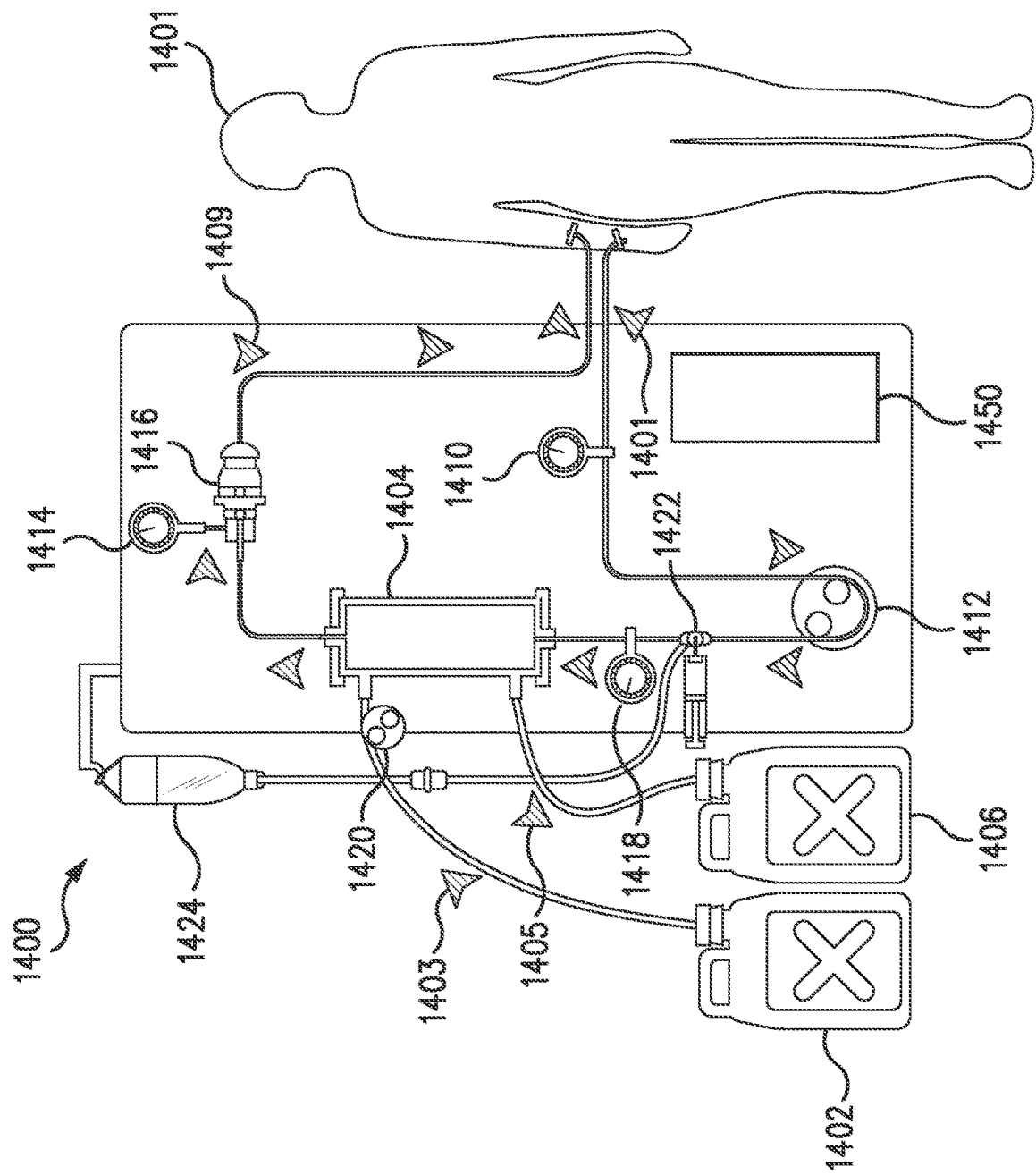
FIG. 14 is a diagram illustrating another exemplary embodiment of a dialysis system in accordance with the present disclosure.

FIGS. 13A-13B show an example of a peritoneal dialysis (PD) system 1301, which is configured in accordance with an exemplary embodiment of the system described herein. In some implementations, the PD system 1301 may be a home PD system, e.g., a PD system configured for use at a patient's home. The dialysis system 1301 may include a dialysis machine 1300 (e.g., a peritoneal dialysis machine 1300, also referred to as a PD cycler) and in some embodiments the machine may be seated on a cart 1304.

The dialysis machine 1302 may include a housing 1306, a door 1308, and a cartridge interface including pump heads 1342, 1344 for contacting a disposable cassette, or cartridge 1315, where the cartridge 1315 is located within a compartment formed between the cartridge interface and the closed door 1308 (e.g., cavity 1305). Fluid lines 1325 may be coupled to the cartridge 1315 in a known manner, such as via a connector, and may further include valves for controlling fluid flow to and from fluid bags including fresh dialysate and warming fluid. In another embodiment, at least a portion of the fluid lines 1325 may be integral to the cartridge 1315. Prior to operation, a user may open the door 1308 to insert a fresh cartridge 1315, and to remove the used cartridge 1315 after operation.

The cartridge 1315 may be placed in the cavity 1305 of the machine 1300 for operation. During operation, dialysis fluid may be flowed into a patient's abdomen via the cartridge 1315, and spent dialysate, waste, and/or excess fluid may be removed from the patient's abdomen via the cartridge 1315. The door 1308 may be securely closed to the machine 1300. Peritoneal dialysis for a patient may include a total treatment of approximately 10 to 30 liters of fluid, where approximately 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

A heater tray 1316 may be positioned on top of the housing 1306. The heater tray 1316 may be any size and shape to accommodate a bag of dialysate (e.g., a 5 L bag of dialysate) for batch heating. The dialysis machine 1300 may also include a user interface such as a touch screen 1318 and control panel 1320 operable by a user (e.g., a caregiver or a patient) to allow, for example, set up, initiation, and/or termination of a dialysis treatment. In some embodiments, the heater tray 1316 may include a heating element 1335, for heating the dialysate prior to delivery into the patient.

Dialysate bags 1322 may be suspended from hooks on the sides of the cart 1334, and a heater bag 1324 may be positioned in the heater tray 1316. Hanging the dialysate bags 1322 may improve air management as air content may be disposed by gravity to a top portion of the dialysate bag 1322. Although four dialysate bags 1322 are illustrated in FIG. 13B, any number "n" of dialysate bags may be connectable to the dialysis machine 1300 (e.g., 1 to 5 bags, or more), and reference made to first and second bags is not limiting to the total number of bags used in a dialysis system 1301. For example, the dialysis machine may have dialysate bags 1322a, . . . 1322n connectable in the system 1301. In some embodiments, connectors and tubing ports may connect the dialysate bags 1322 and lines for transferring dialysate. Dialysate from the dialysate bags 1322 may be transferred to the heater bag 1324 in batches. For example, a batch of dialysate may be transferred from the dialysate bags 1322 to the heater bag 1324, where the dialysate is heated by the heating element 1340. When the batch of dialysate has reached a predetermined temperature (e.g., approximately 98°-100° F., 37° C.), the batch of dialysate may be flowed into the patient. The dialysate bags 1322 and the heater bag 1324 may be connected to the cartridge 1315 via dialysate bag lines or tubing 1325 and a heater bag line or tubing 1328, respectively. The dialysate bag lines 1325 may be used to pass dialysate from dialysate bags 1322 to the cartridge during use, and the heater bag line 1328 may be used to pass dialysate back and forth between the cartridge and the heater bag 1324 during use. In addition, a patient line 1336 and a drain line 1332 may be connected to the cartridge 1315. The patient line 1336 may be connected to a patient's abdomen via a catheter and may be used to pass dialysate back and forth between the cartridge and the patient's peritoneal cavity by the pump heads 1342, 1344 during use. The drain line 1332 may be connected to a drain or drain receptacle and may be used to pass dialysate from the cartridge to the drain or drain receptacle during use.

Although in some embodiments, dialysate may be batch heated as described above, in other embodiments, dialysis machines may heat dialysate by in-line heating, e.g., continuously flowing dialysate through a warmer pouch positioned between heating elements prior to delivery into a patient. For example, instead of a heater bag for batch heating being positioned on a heater tray, one or more heating elements may be disposed internal to the dialysis machine. A warmer pouch may be insertable into the dialysis machine via an opening. It is also understood that the warmer pouch may be connectable to the dialysis machine via tubing (e.g., tubing 1325), or fluid lines, via a cartridge. The tubing may be connectable so that dialysate may flow from the dialysate bags, through the warmer pouch for heating, and to the patient.

In such in-line heating embodiments, a warmer pouch may be configured so dialysate may continually flow through the warmer pouch (instead of transferred in batches for batch heating) to achieve a predetermined temperature before flowing into the patient. For example, in some embodiments the dialysate may continually flow through the warmer pouch at a rate between approximately 100-300 mL/min. Internal heating elements (not shown) may be positioned above and/or below the opening, so that when the warmer pouch is inserted into the opening, the one or more heating elements may affect the temperature of dialysate flowing through the warmer pouch. In some embodiments, the internal warmer pouch may instead be a portion of tubing in the system that is passed by, around, or otherwise configured with respect to, a heating element(s).

The touch screen 1318 and the control panel 1320 may allow an operator to input various treatment parameters to the dialysis machine 1300 and to otherwise control the dialysis machine 1300. In addition, the touch screen 1318 may serve as a display. The touch screen 1318 may function to provide information to the patient and the operator of the dialysis system 1301. For example, the touch screen 1318 may display information related to a dialysis treatment to be applied to the patient, including information related to a prescription.

The dialysis machine 1300 may include a processing module 1302 that resides inside the dialysis machine 1300, the processing module 1302 being configured to communicate with the touch screen 1318 and the control panel 1320. The processing module 1302 may be configured to receive data from the touch screen 1318 the control panel 1320 and sensors, e.g., weight, air, flow, temperature, and/or pressure sensors, and control the dialysis machine 1300 based on the received data. For example, the processing module 1302 may adjust the operating parameters of the dialysis machine 1300.

The dialysis machine 1300 may be configured to connect to a network 1303. The connection to network 1303 may be via a wired and/or wireless connection. The dialysis machine 1300 may include a connection component 1304 configured to facilitate the connection to the network 1303. The connection component 1304 may be a transceiver for wireless connections and/or other signal processor for processing signals transmitted and received over a wired connection. Other medical devices (e.g., other dialysis machines) or components may be configured to connect to the network 1303 and communicate with the dialysis machine 1300.

The user interface portion such as the touch screen 1318 and/or display 1320 may include one or more buttons for selecting and/or entering user information. The touch screen 1318 and/or display 1320 may be operatively connected to a controller (not shown) and disposed in the machine 1300 for receiving and processing the inputs to operate the dialysis machine 1300.

In some embodiments, the machine 1200, 1300, 1400 may wirelessly transmit (e.g., via a wireless Internet connection), alternatively or simultaneously or in coordination with sending information to the integrated care system 220, 220', information or alerts to a remote location, including but not limited to a doctor's office, hospital, call center, and technical support. For example, the machine 1200, 1300, 1400 may provide real time remote monitoring of machine operation and patient parameters. The memory 1220 of the machine 1200, may store data, or the machine 1200, 1300, 1400 may transmit data to a local or remote server at scheduled intervals.

FIG. 14 illustrates a diagram of an exemplary embodiment of a dialysis system 1400 in accordance with the present disclosure. The dialysis system 1400 may be configured to provide hemodialysis treatment to a patient 1401. Fluid reservoir 1402 may deliver fresh dialysate to a dialyzer 1404 via tubing 1403, and reservoir 1406 may receive spent dialysate once it has passed through the dialyzer 1404 via tubing 1405. A hemodialysis operation may filter particulates and/or contaminates from a patient's blood through a patient external filtration device, for example, a dialyzer 1404. As the dialysate is passed through the dialyzer 1404, so too unfiltered patient blood is passed into the dialyzer via tubing 1407 and filtered blood is returned to the patient via tubing 1409. Arterial pressure may be monitored via pressure sensor 1410, inflow pressure monitored via sensor 1418, and venous pressure monitored via pressure sensor 1414. An air trap and detector 1416 may ensure that air is not introduced into patient blood as it is filtered and returned to the patient 1401. The flow of blood and the flow of dialysate are controlled via respective pumps, including a blood pump 1412 and a fluid pump 1420. Heparin 1422, a blood thinner, may be used in conjunction with saline 1424 to ensure blood clots do not form or occlude blood flow through the system.

In some embodiments, the dialysis system 1400 may include a controller 1450, which may be similar to the controller 1405 described above with respect to dialysis machines 1400, 1400. The controller 1450 may be configured to monitor fluid pressure readings to identify fluctuations indicative of patient parameters, such as heart rate and/or respiration rate. In some embodiments, a patient heart rate and/or respiration rate may be determinable by the fluid pressure in the fluid flow lines and fluid bags. The controller 1450 may also be operatively connected to and/or communicate with additional sensors or sensor systems, although the controller 1450 may use any of the data available on the patient's biologic functions or other patient parameters. Dialysis systems may send and/or receive information to the integrated care system 220, 220' for providing appropriate medical treatment to a patient, based on an estimated disease progression.

Figure 15:
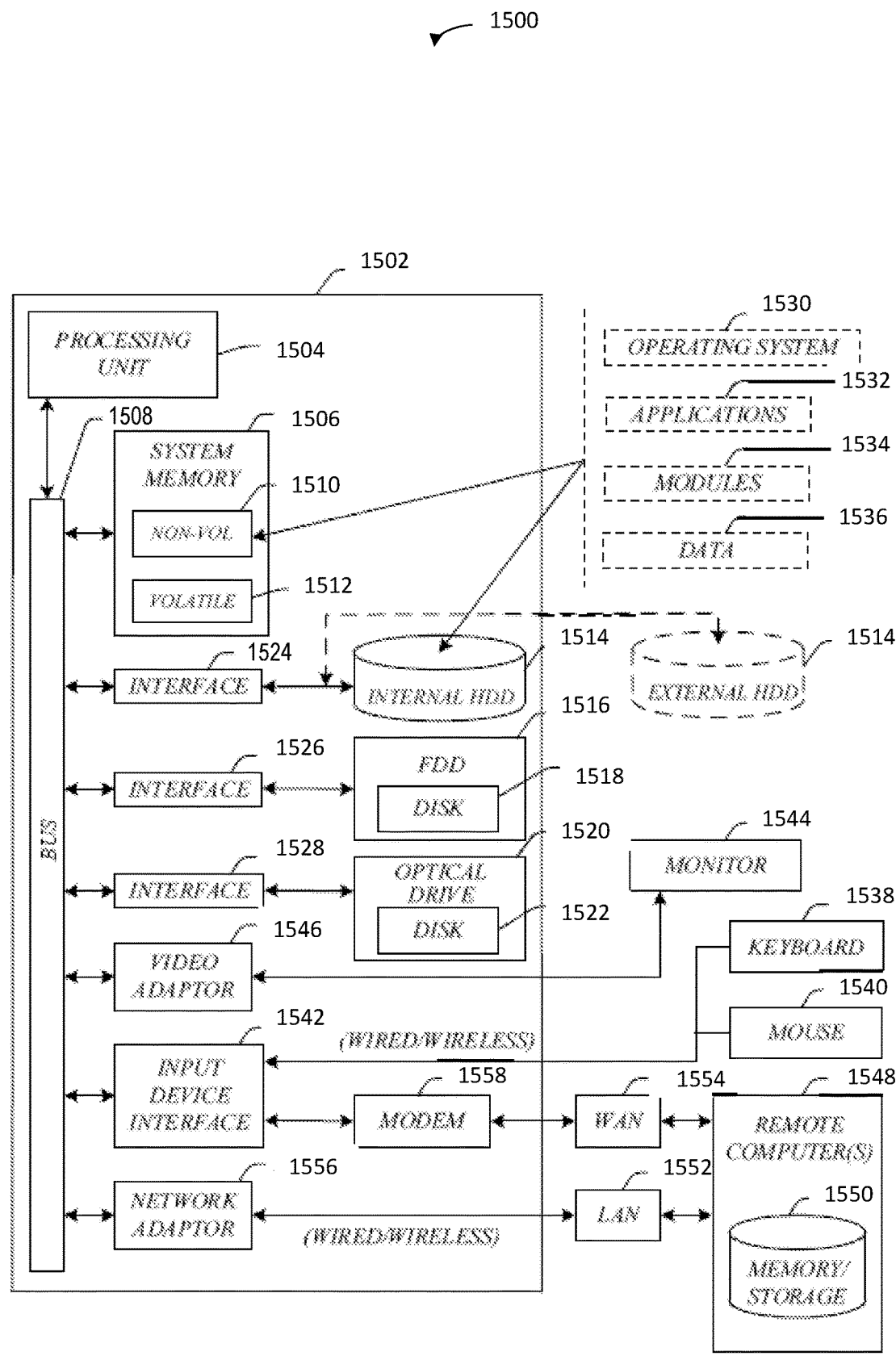
FIG. 15 is a block diagram illustrating an exemplary embodiment of a computing architecture in accordance with the present disclosure.

FIG. 15 illustrates an embodiment of an exemplary computing architecture 1500 suitable for implementing various embodiments as previously described. In various embodiments, the computing architecture 1500 may comprise or be implemented as part of an electronic device. In some embodiments, the computing architecture 1500 may be representative, for example, of computing device 410 and/or components of the platform 505 and/or integrated care system 220, 220'. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 1500. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1500 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1500.

As shown in FIG. 15, the computing architecture 1500 comprises a processing unit 1504, a system memory 1506 and a system bus 1508. The processing unit 1504 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1504.

The system bus 1508 provides an interface for system components including, but not limited to, the system memory 1506 to the processing unit 1504. The system bus 1508 can be any of several types of bus structure that may further interconnect to a memory bus (with or without a memory controller), a peripheral bus, and a local bus using any of a variety of commercially available bus architectures. Interface adapters may connect to the system bus 1508 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1506 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 15, the system memory 1506 can include non-volatile memory 1510 and/or volatile memory 1512. A basic input/output system (BIOS) can be stored in the non-volatile memory 1510.

The computer 1502 may include various types of computer-readable storage media in the form of one or more lower speed memory units, including an internal (or external) hard disk drive (HDD) 1514, a magnetic floppy disk drive (FDD) 1516 to read from or write to a removable magnetic disk 1518, and an optical disk drive 1520 to read from or write to a removable optical disk 1522 (e.g., a CD-ROM or DVD). The HDD 1514, FDD 1516 and optical disk drive 1520 can be connected to the system bus 1508 by a HDD interface 1524, an FDD interface 1526 and an optical drive interface 1528, respectively. The HDD interface 1524 for external drive implementations can include at least one or both of Universal Serial Bus (USB) and IEEE 884 interface technologies.

The drives and associated computer-readable media provide volatile and/or nonvolatile storage of data, data structures, computer-executable instructions, and so forth. For example, a number of program modules can be stored in the drives and memory units 1510, 1512, including an operating system 1530, one or more application programs 1532, other program modules 1534, and program data 1536. In one embodiment, the one or more application programs 1532, other program modules 1534, and program data 1536 can include, for example, the various applications and/or components of system and/or apparatus 200, 200', 220, 220', 400, 500.

A user can enter commands and information into the computer 1502 through one or more wire/wireless input devices, for example, a keyboard 1528 and a pointing device, such as a mouse 1540. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1504 through an input device interface 1542 that is coupled to the system bus 1508, but can be connected by other interfaces such as a parallel port, IEEE 894 serial port, a game port, a USB port, an IR interface, and so forth.

A monitor 1544 or other type of display device is also connected to the system bus 1508 via an interface, such as a video adaptor 1546. The monitor 1544 may be internal or external to the computer 802. In addition to the monitor 1544, a computer typically includes other peripheral output devices, such as speakers, printers, and so forth.

The computer 1502 may operate in a networked environment using logical connections via wire and/or wireless communications to one or more remote computers, such as a remote computer 1548. The remote computer 1548 can be a workstation, a server computer, a router, a personal computer, portable computer, microprocessor-based entertainment appliance, a peer device or other common network node, and typically includes many or all of the elements described relative to the computer 1502, although, for purposes of brevity, only a memory/storage device 1550 is illustrated. The logical connections depicted include wire/wireless connectivity to a local area network (LAN) 1552 and/or larger networks, for example, a wide area network (WAN) 1554. Such LAN and WAN networking environments are commonplace in offices and companies, and facilitate enterprise-wide computer networks, such as intranets, all of which may connect to a global communications network, for example, the Internet.

When used in a LAN networking environment, the computer 1502 is connected to the LAN 1552 through a wire and/or wireless communication network interface or adaptor 1556. The adaptor 1556 can facilitate wire and/or wireless communications to the LAN 1552, which may also include a wireless access point disposed thereon for communicating with the wireless functionality of the adaptor 1556.

When used in a WAN networking environment, the computer 1502 can include a modem 1558, or is connected to a communications server on the WAN 1554, or has other means for establishing communications over the WAN 1554, such as by way of the Internet. The modem 1558, which can be internal or external and a wire and/or wireless device, connects to the system bus 1508 via the input device interface 1542. In a networked environment, program modules depicted relative to the computer 1502, or portions thereof, can be stored in the remote memory/storage device 1550. It will be appreciated that the network connections shown are exemplary and other means of establishing a communications link between the computers can be used.

The computer 1502 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Some embodiments of the disclosed systems may be implemented, for example, using a storage medium, a computer-readable medium or an article of manufacture which may store an instruction or a set of instructions that, if executed by a machine (i.e., processor or microcontroller), may cause the machine to perform methods and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

To the extent used in this description and in the claims, a recitation in the general form of "at least one of [a] and [b]" should be construed as disjunctive. For example, a recitation of "at least one of [a], [b], and [c]" would include [a] alone, [b] alone, [c] alone, or any combination of [a], [b], and [c].

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A computer-implemented method for administering at least one clinical intervention to treat chronic kidney disease, comprising:

accessing historic estimated glomerular filtration rate (eGFR) values of the patient that vary as a function of a progression of the chronic kidney disease over time;

determining a trend of a future progression of the chronic kidney disease for the patient based on the historic eGFR values;

determining predicted future eGFR values for the patient based on the trend;

generating a visual chart configured for presentation on a display of a computing device, the visual chart comprising the historic eGFR values, a trend line corresponding to the trend, and the future eGFR values arranged along the trend line;

based on the trend, automatically providing at least one marker on the trend line that identifies the at least one clinical intervention and a time in the future when the at least one clinical intervention is expected to be needed; and based on the at least one marker, administering the at least one clinical intervention to the patient.

2. The method of claim 1, further comprising executing clinical preparations at a time prior to administering the at least one clinical intervention to the patient, wherein the executing clinical preparations includes providing treatment options to the patient and executing the intervention according to a corresponding treatment decision made by the patient.

3. The method of claim 1, wherein the trend is computationally estimated by non-linear regression.

4. The method of claim 1, wherein the trend is computationally estimated by linear regression.

5. The method according to claim 1, wherein the at least one clinical intervention comprises at least one of education, nutritional counseling, vaccinations, referral to nephrology, referral for renal transplant, referral for permanent access, and starting dialysis.

6. The method according to claim 1, further comprising:
accessing a database comprising intervention information, the intervention information indicating eGFR values and associated clinical interventions; and
providing the at least one marker based on the trend and the intervention information.

7. The method according to claim 1, further comprising determining updated historic eGFR values determined after administration of the at least one clinical intervention.

8. The method according to claim 7, further comprising presenting an updated chart determined based on an updated trend line generated using the updated historical eGFR values.

9. The method according to claim 7, wherein the administration of the at least one clinical intervention causes a change in at least a portion of the predicted eGFR values presented on the updated chart.

10. A computer-implemented method for treating progression of chronic kidney disease in a patient, the method comprising, via at least one processor of at least one computing device:

accessing historic estimated glomerular filtration rate (eGFR) values of the patient that vary as a function of a progression of the chronic kidney disease over time;

determining a trend of a future progression of the chronic kidney disease for the patient based on the historic eGFR values;

calculating predicted future eGFR values for the patient based on the trend;

accessing a database comprising intervention information, the intervention information indicating eGFR values and associated clinical interventions;

based on the trend and the intervention information, automatically providing at least one marker on the trend line that identifies the at least one clinical intervention and a time in the future when the at least one clinical intervention is expected to be needed; and transmitting an alert, determined based on the chart, to a device communicatively coupled to the at least one computing device indicating an upcoming date when the at least one clinical intervention is necessary for the patient.

11. The method according to claim 10, wherein the at least one marker is automatically provided at a location relative to the trend that corresponds to predetermined values of historic eGFR values.

12. The method according to claim 10, wherein the historic eGFR values are determined based on information received from a remote source, the information received being at least one of the historic eGFR values of the patient and data for calculating the historic eGFR values for the patient.

13. The method according to claim 10, wherein the at least one clinical intervention comprises at least one of education, nutritional counseling, vaccinations, referral to nephrology, referral for renal transplant, referral for permanent access, and starting dialysis.

14. The method according to claim 10, further comprising:
calculating actual eGFR values for the patient;
comparing the actual values to the predicted future values; and
adjusting the treatment options in response to a deviation between the actual values and the predicted future values.

* * * * *

UNITED STATES PATENT AND TRADEMARK OFFICE
CERTIFICATE OF CORRECTION

PATENT NO. : 11,026,625 B2
APPLICATION NO. : 16/058965
DATED : June 8, 2021
INVENTOR(S) : Blanchard et al.

Page 1 of 1

It is certified that error appears in the above-identified patent and that said Letters Patent is hereby corrected as shown below:

In the Claims

Claim 9: Column 32, Line 1: "predicted eGFR values" should read as -- future eGFR values --.

Claim 9: Column 32, Line 2: "the updated chart" should read as -- the visual chart. --.

Claim 10: Column 32, Line 19: "marker on the" should read as -- marker on a --.

Claim 10: Column 32, Line 20: "identifies the at least one" should read as -- identifies at least one --.

Claim 10: Column 32, Line 23: "based on the chart" should read as -- based on a chart --.

Signed and Sealed this
Fourteenth Day of October, 2025

John A. Squires
*Director of the United States Patent and Trademark Office*